(12) United States Patent
Casar et al.

(10) Patent No.: US 8,183,397 B2
(45) Date of Patent: May 22, 2012

(54) SYNTHESIS OF STATINS

(75) Inventors: Zdenko Casar, Logatec (SI); Tomaz Mesar, Trzin (SI); Gregor Kopitar, Radomlje (SI); Peter Mrak, Zabnica (SI); Matej Oslaj, Kranj (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 159 days.

(21) Appl. No.: 12/594,302

(22) PCT Filed: Apr. 2, 2008

(86) PCT No.: PCT/EP2008/053904
§ 371 (c)(1),
(2), (4) Date: Mar. 8, 2010

(87) PCT Pub. No.: WO2008/119810
PCT Pub. Date: Oct. 9, 2008

(65) Prior Publication Data
US 2011/0178295 A1     Jul. 21, 2011

(30) Foreign Application Priority Data

Apr. 3, 2007  (EP) .................................... 07105519
Jul. 16, 2007  (EP) .................................... 07112529

(51) Int. Cl.
*C07D 309/10*   (2006.01)
*C07D 239/42*   (2006.01)
(52) U.S. Cl. ........................................ 549/417; 544/297
(58) Field of Classification Search .................. 549/417; 544/297
See application file for complete search history.

(56) References Cited

U.S. PATENT DOCUMENTS

| 4,625,039 | A | 11/1986 | Jewell, Jr. | |
| 5,527,916 | A | 6/1996 | Blacker et al. | |
| 2007/0093660 | A1 | 4/2007 | Tararov et al. | |
| 2008/0249306 | A1* | 10/2008 | Tararov et al. | 544/297 |
| 2008/0300406 | A1* | 12/2008 | Casar | 544/297 |

FOREIGN PATENT DOCUMENTS

| WO | WO-2005/047276 A2 | 5/2005 |
| WO | WO 2005/092867 A | 10/2005 |
| WO | WO-2005/118794 A2 | 12/2005 |
| WO | WO-2006/067456 A2 | 6/2006 |
| WO | WO-2006/134482 A1 | 12/2006 |
| WO | WO-2007/007119 A1 | 1/2007 |

OTHER PUBLICATIONS

Gijsen, Harrie J. M., et al., "Sequential Three- and Four-Substrate Aldol Reactions Catalyzed by Aldolases"; Journal of the American Chemical Society, vol. 117, No. 29; Jul. 26, 1995; pp. 7585-7591.
H.J.M. Gijsen et al., "Unprecedented Asymmetric Aldol Reactions with Three Aldehyde Substrates Catalyzed by 2-Deoxyribose-5-phosphate Aldolase", Journal of the American Chemical Society, 1994, pp. 8422-8423, vol. 116.
Bennett et al., Methyl (3R)-3-hydroxyhex-5-enoate as a precursor to chiral mevinic acid analogues, J. Chem. Soc. Perkin Trans. 1, 1991, pp. 133-140.
Greenberg et al., Development of an efficient, scalable, aldolase-catalyzed process for enantioselective synthesis of statin intermediates, PNAS, 101(16), 2004, p. 4788.
Sambrook and Russell, Molecular Cloning: A Laboratory Manual, 3rd Ed., Cold Spring Harbor, NY 2001.

* cited by examiner

*Primary Examiner* — Andrew D Kosar
*Assistant Examiner* — Karen Cheng
(74) *Attorney, Agent, or Firm* — Arent Fox LLP

(57) ABSTRACT

The process for the synthesis of statins featuring the use of an early intermediate (4R,6S)-6-(dialkoxymethyl)tetrahydro-2H-pyran-2,4-diol which already possesses the desired stereochemistry corresponding to the final statin.

15 Claims, No Drawings

SYNTHESIS OF STATINS

CROSS-REFERENCE TO RELATED APPLICATION

This application is the National Stage of International Application No. PCT/EP2008/053904, filed Apr. 2, 2008, now WO 2008/119810, published Oct. 9, 2008, which claims benefit under 35 U.S.C. 119(a)-(d) or (f) or 365(b) of foreign application EP 07105519.8, filed Apr. 3, 2007, and EP 07112529.8, filed Jul. 16, 2007, the contents of which are incorporated herein by reference in their entirety.

SEQUENCE LISTING

The instant application contains a Sequence Listing which has been submitted via EFS-Web and is hereby incorporated by reference in its entirety. Said ASCII copy, created on Apr. 12, 2010, is named 03030800.txt and is 72,589 bytes in size.

FIELD OF THE INVENTION

The present invention relates in general to the field of chemical technology and in particular to a process for the preparation of HMG-CoA reductase inhibitors, known also as statins, particularly to rosuvastatin. Specifically this invention relates to a preparation of a general but unique intermediate which can be used for the preparation of all statins.

BACKGROUND OF THE INVENTION

Statins, of which the representative examples may be selected from rosuvastatin, cerivastatin, atorvastatin, fluvastatin, pitavastatin, bervastatin, dalvastatin or their analogs or pravastatin, simvastatin, lovastatin or their analogs share a characteristic structure, consisting of respectively a heptenoic or heptanoic acid moiety (free acid, salt or lactone) connected to the aromatic or alicyclic core. Biological activity of statins is closely related to their stereochemistry, especially configuration at the chiral atoms of said heptenoic or heptanoic acid moiety.

Document U.S. Pat. No. 5,527,916 describes a process for the separation of at least one isomer from a mixture of isomers of a tetrahydropyran-2-one having at least two chiral centers.

WO 2005/092867 A2 discloses the use of different lactone derivatives in the preparation of statins, particularly rosuvastatin.

Sequential aldol reactions catalyzed by deoxyribose aldolase are described in J. Am. Chem. Soc. 117, 29, (1995) p. 7585.

An asymmetric aldol reaction with three differently substituted acetaldehyde substrates catalyzed by 2-deoxy-ribose-5-phosphate aldolase (DERA) shows that not all acetaldehyde derivatives are equally accepted as substrates for DERA (J. Am. Chem. Soc. 116 (1994), p. 8422-8423). The reaction time of the enzymatic catalysis was 6 days. The resulting lactone was oxidized with $Br_2$ and $BaCO_3$.

In WO 2006/134482 A1, a 2-deoxyribose-5-phosphate aldolase (DERA) catalyzed aldol addition step is included in a process for forming atorvastatin. The aldolase belongs to the class EC 4.1.2.4.

WO 05/118794 deals with an improvement of the DERA enzyme. The isolated mutant enzymes may be used for the preparation of a 2,4-dideoxyhexose or a 2,4,6-trideoxyhexose having a high variety of substituents.

The object of the present invention is to provide valuable intermediate compounds and processes as building blocks for effectively producing statins.

A further object of the invention is to produce intermediate compounds with inexpensive starting materials and simple equipment.

DISCLOSURE OF THE INVENTION

The object is solved by providing (4R,6S)-4-hydroxy-6-(dialkyloxymethyl)-tetrahydro-2H-pyran-2-ol, which is protected or not protected at the 4-hydroxy position. This compound can be prepared by two different processes, either by a synthetic process or by an enzymatic process.

The relevant synthetic process requires more synthetic steps compared to the enzymatic process however it was utilized to prepare a standard compound which confirmed the structure of the enzymatic product.

The significant enzymatic process allows a one step synthesis with relatively short reaction times and a high yield, and the product has a high stereochemical purity concerning diastereoisomeric excess. Further, according to the present invention, the above mentioned pyran-derivative can be produced from inexpensive starting materials and simple equipment.

One aspect of the invention is a process for preparing a compound of formula IV or V

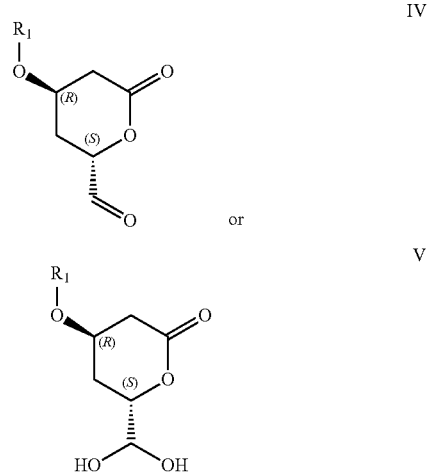

wherein $R_1$ is a protecting group which comprises the following steps:

a) converting a compound of formula I'

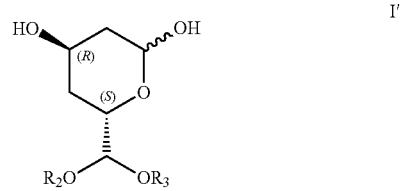

wherein $R_2$ and $R_3$ are independently selected from $C_1$-$C_4$-alkyl or together form a cyclic structure of formula $(CH_2)_n$ wherein n is from 2 to 6,
into a compound of formula II

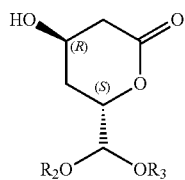

II wherein $R_2$ and $R_3$ are defined as above;

b) subsequently converting said compound obtained in step (a) into a compound of formula III

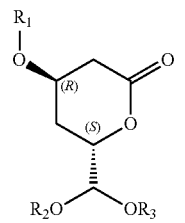

III wherein $R_1$ is a protecting group, $R_2$ and $R_3$ are defined as above, and;

c) subsequently cleaving the acetal-compound of formula III obtained in step (b). This process provides a short and efficient 3-step synthesis to arrive at compounds of formula IV or V.

Preferably the substrate of step (a) is selected from a compound of formula I', wherein $R_2$ and $R_3$ are methyl. The reactants for the oxidation step (a) should be inexpensive and afford a high yield. Thus the oxidation is performed preferably with $Br_2$ and $BaCO_3$.

Step (b) is preferably performed by introducing $R_1$ being a silyl protecting group. Furthermore it is preferred to perform step (b) with tert-butylmethylsilyl chloride.

Preferably step (c) of the process is performed with $I_2$ and acetone. In particular, step (c) is performed in an anhydrous medium to provide the aldehyde compound of formula IV. However the hydrate form V is preferred for isolation and storage. Therefore furthermore it is preferred to perform step (c) in a solvent containing water to provide the hydrate compound of formula V.

Another aspect of the invention is a process for providing the compound of formula IV

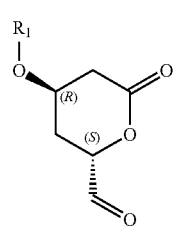

IV wherein $R_1$ is a protecting group,
characterized by providing the compound of formula V

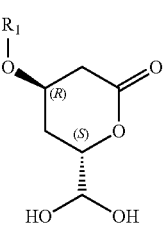

V wherein $R_1$ is a protecting group,
dissolved in a solvent selected from the group of aromatic hydrocarbons, aliphatic hydrocarbons, chlorinated aromatic or aliphatic hydrocarbons and aliphatic ethers. In particular, the solvent of this process is selected from toluene, heptane, methylcyclohexane, cyclohexane, hexane, pentane, dichloromethane, chloroform, 2-chlorotoluene, 3-chlorotoluene, 4-chlorotoluene, $^tBuMeO$, $Et_2O$, $Me_2O$ and THF. This group of solvents favours the provision of the aldehyde of formula IV in an equilibrium of the compounds of formula IV and V. Thus the hydrate form of formula V can be converted to the aldehyde of formula IV without being isolated, but by carrying out the reaction in said solvents.

A further aspect of the invention is a use of any of the compounds of formula I

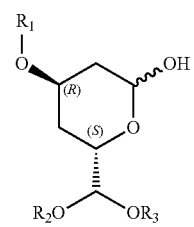

I wherein $R_1$ is H or protecting group; and
$R_2$ and $R_3$ are independently selected from $C_1$-$C_4$-alkyl
for the synthesis of a compound of formula IV or V

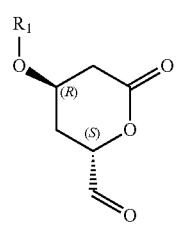

IV or

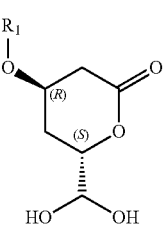

V wherein $R_1$ is H or a protecting group.

Another aspect of the present invention is a compound of formula I,

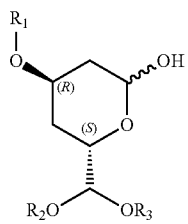

wherein $R_1$ is H or a protecting group; and $R_2$ and $R_3$ are independently selected from $C_1$-$C_4$-alkyl, or together form a cyclic structure of formula $(CH_2)_n$ wherein n is from 2 to 6. The compound of formula I wherein $R_1$ is H or tert-butyldimethylsilyl is preferred. In particular, $R_2$ and $R_3$ are methyl.

Another aspect of the present invention is a process for preparing a lactol compound of formula I'

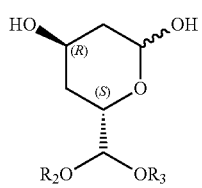

wherein $R_2$ and $R_3$ are independently selected from $C_1$-$C_4$-alkyl, or together form a cyclic structure of formula $(CH_2)_n$ wherein n is from 2 to 6,
which comprises the step of reacting a substrate of formula X

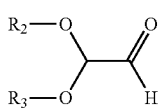

wherein $R_2$ and $R_3$ are defined as above, with acetaldehyde under aldolase-catalysed aldol condensation conditions to form the corresponding lactol compound I'. Preferably this process comprises the additional steps of:
a) converting said lactol compound of formula I' into compound of formula IV

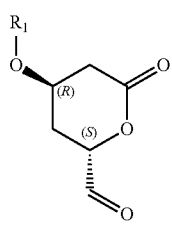

b) subjecting said compound obtained in step (a) to conditions sufficient to produce a statin or a pharmaceutically acceptable salt thereof. Preferably the statin of step (b) is rosuvastatin. More preferably the acceptor substrate X is selected from the group consisting of: 2,2-dimethoxy ethanal, 2,2-diethoxyethanal, 2,2-dipropoxyethanal, 2,2-dibutoxyethanal, 1,3-dioxolane-2-carbaldehyde, 4-methyl-1,3-dioxolane-2-carbaldehyde, 4-ethyl-1,3-dioxolane-2-carbaldehyde, 4-propyl-1,3-dioxolane-2-carbaldehyde, 4-butyl-1,3-dioxolane-2-carbaldehyde, 4,5-dimethyl-1,3-dioxolane-2-carbaldehyde. By using aldolase-catalysed aldol condensation conditions, the number of reaction steps to arrive at IV can be reduced.

It is preferred that the aldolase catalyzing the aldol condensation is 2-deoxyribose-5-phosphate aldolase (DERA). It may be useful to screen different types of DERA enzymes in order to find an enzyme having broader substrate specificity. Furthermore a DERA enzyme may be tailored for a specific substrate. For these reasons different mutant DERA enzymes may be tested. More particularly said aldolase is selected from the group consisting of DERA 01, DERA 02, DERA 03, DERA 04, DERA 05, DERA 06, DERA 07, DERA 08, DERA 09, DERA 10, DERA 11, DERA 12, DERA 13, DERA 14, DERA 15, DERA 16, DERA 17, DERA 18, DERA 19, DERA 20, DERA 21, DERA 22, DERA 23 or an aldolase having an amino acid sequence identity of at least about 70% to amino acid sequence of any of said aldolases. More particularly said aldolase is selected from the group consisting of an aldolase having an amino acid sequence identity of at least about 70% to amino acid sequence of SEQ ID NO: 2, an aldolase having an amino acid sequence identity of at least 90% to amino acid sequence of SEQ ID NO: 5 or an aldolase having an amino acid sequence identity of at least 90% to amino acid sequence of SEQ ID NO: 17.

The process aspect of the invention can be effectively accomplished in reaction conditions wherein a buffer having no primary, secondary or tertiary amino group is used. Such a buffer provides higher yields and less impurities, because it does not undergo chemical reactions with condensation reaction intermediates. In particular the buffer is a phosphate buffer. Preferably the pH value for the aldolase-catalysed aldol condensation is maintained in the range from 6 to 10. More preferably the pH is maintained with a buffer in the range of 7 to 9. In particular the process comprises the steps of
i) performing the aldolase-catalysed aldol condensation in an aqueous medium at a pH value of 7 to 9 at a temperature of 30-50° C. to form a reaction mixture,
ii) maintaining said reaction mixture at said temperature and pH value for a time period between 1 h and 6 h; and
iii) recovering said compound of formula I'.

A further aspect of the invention is a use of aldolase for the reaction of a substrate of the formula X

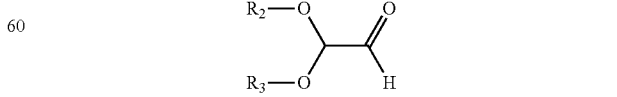

wherein $R_2$ and $R_3$ are independently selected from $C_1$-$C_4$-alkyl, or together form a cyclic structure of formula $(CH_2)_n$ wherein n is from 2 to 6, with acetaldehyde under aldolase-catalysed aldol condensation conditions to form the corresponding lactol compound of the formula I'

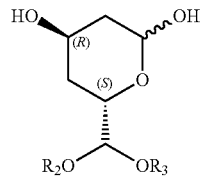

wherein $R_2$ and $R_3$, wherein $R_2$ and $R_3$ are defined as above. In particular said aldolase is 2-deoxyribose-5-phosphate aldolase (DERA). More particularly aldolase is selected from the group consisting of DERA 01 to DERA 23 as described above. In particular said aldolase is comprised within a living whole cell, or is comprised within an inactivated whole cell, or is comprised within a homogenized whole cell, or is comprised within a cell free extract, or is a purified enzyme, or is immobilized, or is in a form of an extracelularly expressed protein.

Another aspect of the invention is a process for preparing a HMG CoA reductase inhibitor, characterized in that the compound of formula I'

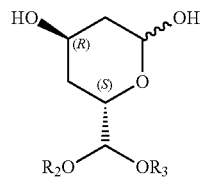

wherein $R_2$ and $R_3$ are independently selected from $C_1$-$C_4$-alkyl or together form a cyclic structure of formula $(CH_2)_n$ wherein n is from 2 to 6, is provided as an intermediate compound to prepare said HMG CoA reductase inhibitor.

Preferably the process comprises the following steps:

I) converting compound I' into a compound of formula IV

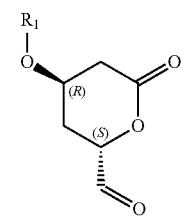

wherein $R_1$ is a protecting group; and

II) reacting said compound of formula IV under conditions sufficient to produce a HMG CoA reductase inhibitor or a pharmaceutically acceptable derivative thereof. More preferably the conditions of step (II) are set by a Wittig coupling with an appropriate phosphonium salt to give rosuvastatin or a derivative thereof, preferably wherein the process comprises the steps of:

IIa) providing a phosphonium salt having the formula VI

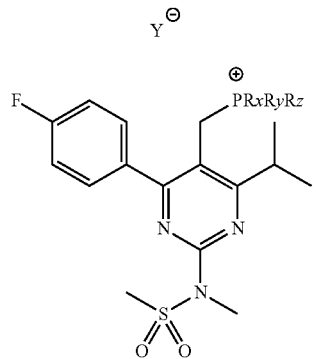

wherein Rx, Ry, and Rz, are the same or different and are selected from optionally substituted $C_1$-$C_8$-alkyl or $C_3$-$C_6$-cycloalkyl or $C_1$-$C_8$-alkenyl or $C_5$-$C_6$-cycloalkenyl or aryl, and Y is an anion, preferably halogen or RCOO⁻ anion, more preferably chloride, bromide or trifluoroacetate;

to give a compound of formula VII

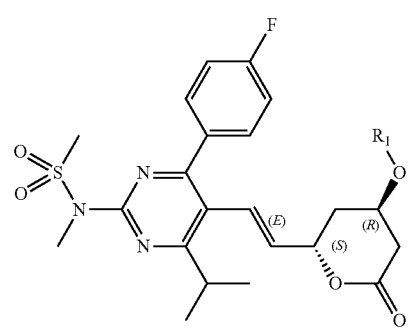

and

IIb) subsequently converting the compound VII to rosuvastatin or a salt thereof.

In this process, it is preferred that $R_2$ and $R_3$ are methyl.

Yet another aspect of the invention is a process for preparing a HMG CoA reductase inhibitor, wherein the compound of formula II

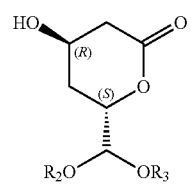

wherein $R_2$ and $R_3$ are independently selected from $C_1$-$C_4$-alkyl or together form a cyclic structure of formula $(CH_2)_n$ wherein n is from 2 to 6 is provided as an intermediate compound to prepare said HMG CoA reductase inhibitor, which process comprises the steps of:

A) converting a compound of formula II into a compound of formula IV

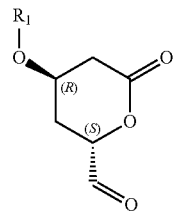

IV wherein $R_1$ is a protecting group; and

B) reacting said compound of formula IV by a Wittig coupling with an appropriate phosphonium salt to give a HMG CoA reductase inhibitor. Preferably the HMG CoA reductase inhibitor is rosuvastatin or a derivative thereof. Furthermore, it is preferred that $R_2$ and $R_3$ are methyl. Rosuvastatin or a derivative thereof includes a free acid form, a salt form such as sodium, potassium or especially calcium salt, and e.g. acid esters or lactone rings, but is not limited thereto.

DETAILED DESCRIPTION OF THE INVENTION

The present invention relates in general to the synthesis of HMG CoA reductase inhibitors (statins) wherein the compound of formula IV

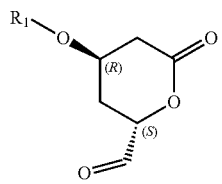

IV wherein $R_1$ is a protecting group, is reacted with an appropriate phosphonium salt, phosphinoxide or phosphonate of the heterocyclic or alicyclic skeleton of a statin, such as a compound of formula VI

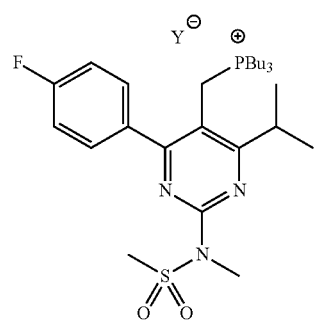

VI wherein Y is a suitable anion.

The compound IV (in particular IV' wherein $R_1$ is tent-butyldimetylsilyl) is prepared from an intermediate I' ($R_2$ and $R_3$ are independently selected from $C_1$-$C_4$-alkyl, or together form a cyclic structure of formula $(CH_2)_n$ wherein n is from 2 to 6) in accordance with the following general scheme:

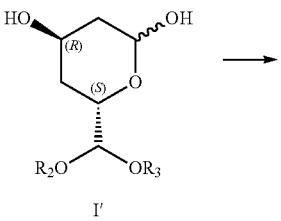

I'

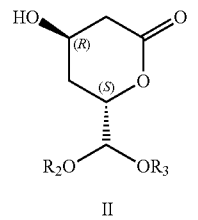

II

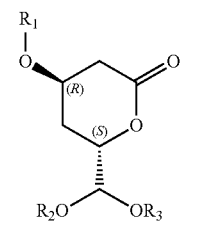

III

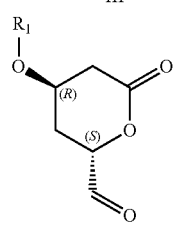 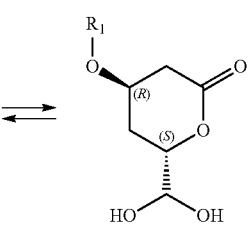

IV    V or specific for I'' wherein $R_2$ and $R_3$ are both Me, shown in the following scheme:

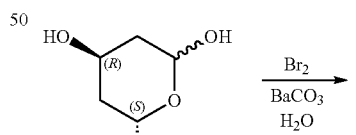

I''

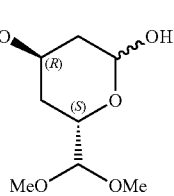 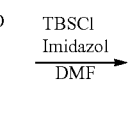

II'

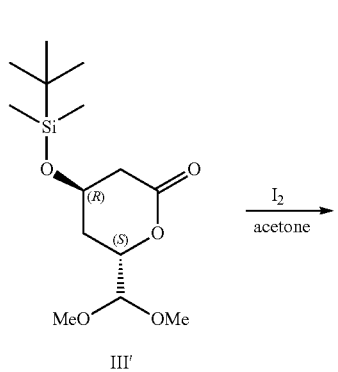

III'

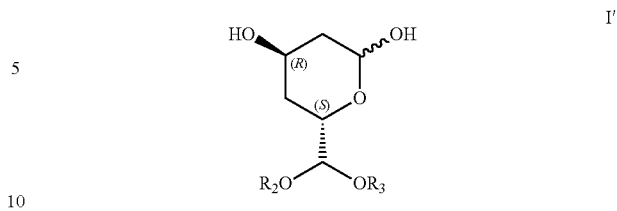

wherein $R_2$ and $R_3$ are independently selected from $C_1$-$C_4$-alkyl, or together form (an optionally $C_1$-$C_4$-alkyl substituted) cyclic structure of formula $(CH_2)_n$ wherein n is from 2 to 6.

The protecting group $R_1$ of the present invention may be any conventionally used protecting group, in particular alkyl, acyl, silyl or similar group, more particularly selected from acetyl (Ac), pivaloyl (Piv), p-toluenesulfonyl (TOS), p-methoxyethoxymethyl ether (MEM), methoxymethyl ether (MOM), p-methoxybenzyl ether (PMB), methylthiomethyl ether, t-butyl, tetrahydropyranyl (THP), benzyl (Bn), diphenylmethyl or triphenylmethyl group, preferably silyl protecting group which can be represented by a formula $SiR_1R_2R_3$ in which $R_1$, $R_2$, $R_3$ are independently selected from alkyl (preferably $C_1$-$C_6$) or aryl (preferably $C_5$-$C_{10}$), such as $SiMe_3$ (TMS), $SiMe_2^tBu$ (TBDMS), $Si(i\text{-}Pr)_3$ (TIPS), $SiPh_2^tBu$, $SiMe_2Ph$.

The feature of an early intermediate I', which is chemically (4R,6S)-6-(dialkoxymethyl)-tetrahydro-2H-pyran-2,4-diol or (4R,6S)-6-(alkylenedioxy)tetrahydro-2H-pyran-2,4-diol and in particular I", which is chemically (4R,6S)-6-(dimethoxymethyl)-tetrahydro-2H-pyran-2,4-diol, is that it possesses the desired stereochemistry, avoiding subsequent separations of later intermediates. On the other hand I' or I" is chemically aldehyde acetal which behaves as a masked (protected) aldehyde which eliminates the necessity for the oxidation step in the synthesis of statins.

Compounds IV and IV', or hydrate thereof, obtained from I" or I' can be further used to prepare rosuvastatin as outlined on the following scheme:

IV'

Furthermore the present invention provides for an enzymatic synthesis of intermediate I', which is chemically (4R, 6S)-6-(dialkoxymethyl)tetrahydro-2H-pyran-2,4-diol or (4R,6S)-6-(alkylenedioxy)tetrahydro-2H-pyran-2,4-diol of a general formula I'

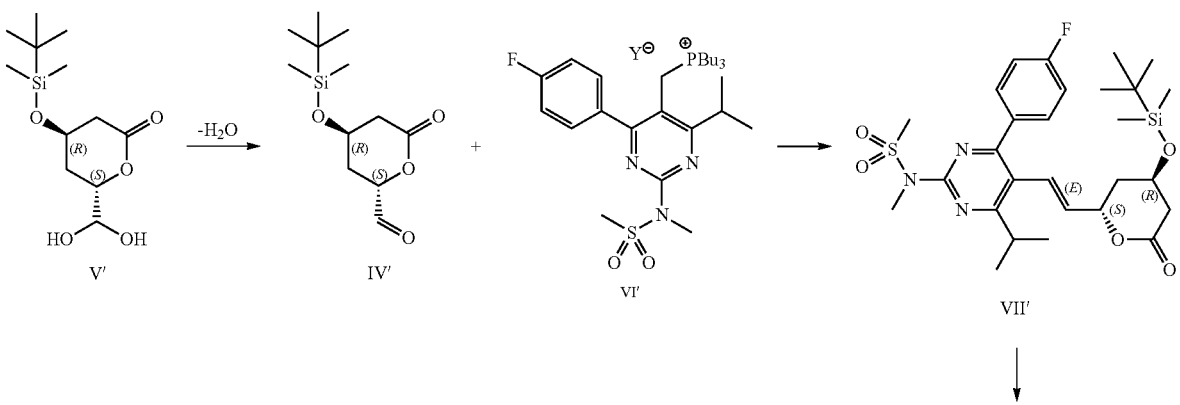

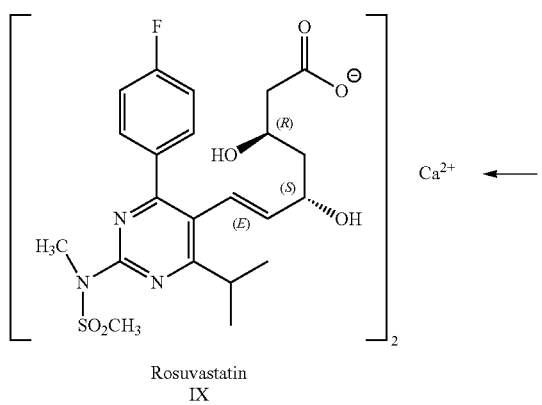

Rosuvastatin
IX

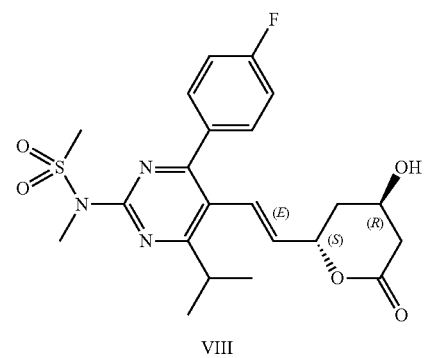

VIII

To produce other statins, the (2S,4R)-4-(protected)-6-oxo-tetrahydro-2H-pyran-2-carbaldehyde IV or its hydrate V should be reacted under the condition of a Wittig coupling with an appropriate reagent followed by hydrogenation when needed.

The appropriate reagent is a heterocylic or alicyclic derivative (skeleton of statin) of a following formula:

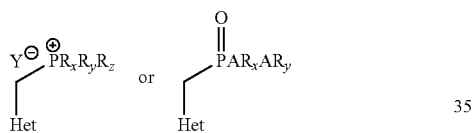

wherein A can be a bond or O;

and wherein $R_x$, $R_y$, and $R_z$, are the same or different and are selected from optionally substituted $C_1$-$C_8$-alkyl or $C_3$-$C_6$-cycloalkyl or $C_1$-$C_8$-alkenyl or $C_5$-$C_6$-cycloalkenyl or aryl;

and Y is an anion, preferably halogen or $RCOO^-$ anion, more preferably chloride, bromide or trifluoroacetate;

and Het is selected so that it forms a heterocyclic or alicyclic skeleton of a statin; other HMG-CoA reductase inhibitors (preferably selected among cerivastatin, fluvastatin, pitavastatin, bervastatin, dalvastatin) can be analogously prepared.

The heterocyclic or alicyclic skeleton (Het) of statins is in particular selected from:

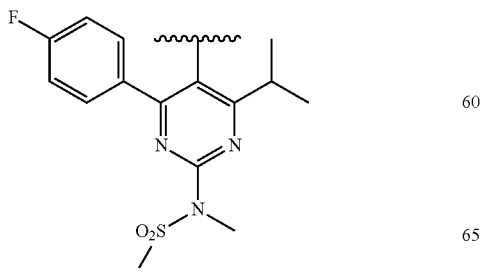

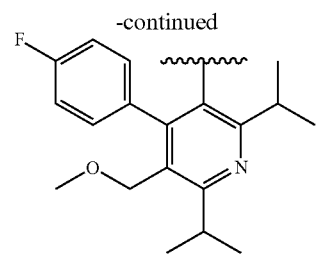

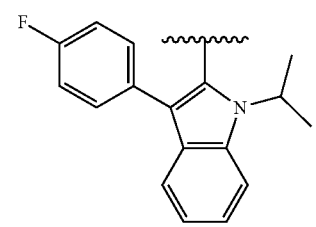

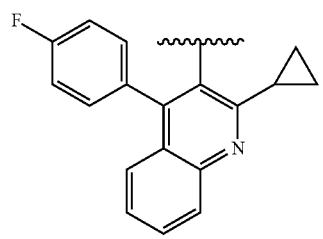

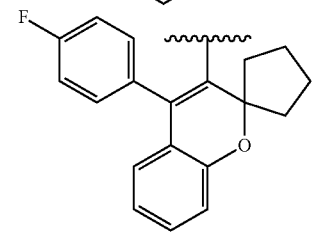

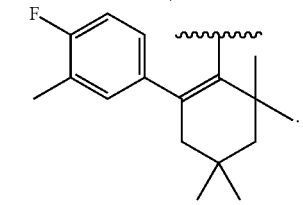

Compounds IV or IV' may in the presence of water, if in a liquid state or dissolved in an organic solvent, exist in an equilibrium with its hydrated form V (or V')

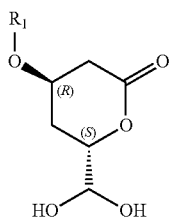

V and may be isolated in an aldehyde or a hydrate form. The aldehyde form can be isolated from anhydrous media by evaporation while the hydrate form can be isolated from solvents containing water by evaporation or precipitation and filtration. The hydrate form is preferable for isolation and storage. The Witting reaction proceeds with the aldehyde form, however both forms can be used if the reaction is carried out in a solvent in which the aldehyde form is favoured in the equilibrium. In chlorinated hydrocarbons (such as chloroform, dichloromethane), hydrocarbons (such as hexane and cyclohexane) and particularly in aromatic hydrocarbons (such as toluene or the chlorinated analogue thereof), the equilibrium is shifted completely towards the aldehyde form. The use of toluene as the solvent for the Wittig reaction (with phosphonium salt, phosphinoxide or phosphonate of heterocyclic or alicyclic skeleton of a statin) significantly increases the yield compared to the commonly used THF because in THF aldehyde and hydrate are present in approximately equal amounts while aromatic hydrocarbons favour the aldehyde.

In general, I" can be converted to II" ((4R,6S)-6-(dimethoxymethyl)-4-hydroxytetrahydro-2H-pyran-2-one) or I' to analogous II ((4R,6S)-6-(dialkoxymethyl)-4-hydroxytetrahydro-2H-pyran-2-one) or ((4R,6S)-6-(alkylenedioxymethyl)-4-hydroxytetrahydro-2H-pyran-2-one) by oxidation with a suitable oxidizing agent which can be selected from bromine, N-iodosuccinimide/tetra-n-butylammonium iodide in dichloromethane or NaOCl in an appropriate solvent, in particular with bromine in the presence of weak bases, in particular $BaCO_3$ which does not hydrolize the formed lactone in a suitable solvent which can be polar and protic, such as water at temperatures from 0 to 40° C. The reaction proceeds well if there is an excess of bromine compared to the substrate and excess of $BaCO_3$ compared to the bromine. The product is conveniently isolated by extraction from water with a water immiscible solvent, such as ethyl acetate, followed by flash chromatography.

To II' or II, a suitable protecting group, which can be any conventionally used protecting group, in particular silyl protecting group, is introduced, in particular by a reaction with tert-butyldimethylsilyl chloride. The reaction is conveniently done in the presence of a base, selected from amines, imidazoles and pyridines, preferably imidazole in solvents selected from amides: N,N-dimethylformamide (DMF), N,N-dimethylacetamide (DMA), hexamethylphosphor triamide (HMPTA); N-methylpyrrolidone (NMP); N,N'-dimethylpropyleneurea (DMPU); N,N,N',N'-tetramethylurea (TMU); dimethylsulfoxide (DMSO); nitriles (acetonitrile), chlorinated hydrocarbons (dichloromethane, chloroform), aromatic hydrocarbons (toluene), preferably in DMF where starting material and reagents are well soluble. The reaction can be performed at temperatures between −10° C. to 30° C. Preferably at 0° C. The reaction is accomplished in a period from one hour up to a day, preferably in 12 to 24 hours. The product (III' or III) can be isolated by evaporation of the chlorinated hydrocarbon solvent followed by flash chromatography or by dilution with water and extraction to a water immiscible solvent, such as ethyl acetate, followed by evaporation when amide solvent is used for the reaction.

III' can be converted to IV' (or III to IV) by a hydrolytic cleavage of acetals by acid catalysts which do not catalyse the cleavage of lactone by using Broensted or Lewis acids in an organic solvent, preferably Lewis acids, such as $FeCl_3 \cdot 6H_2O$, $FeCl_3 \cdot SiO_2$, $CuCl_2 \cdot 2H_2O$, $Zn(NO_3)_2 \cdot 6H_2O$, $(NH_4)_2Ce(NO_3)_6$, $CeCl_3 \cdot 7H_2O$, $TiCl_4$, $ZnBr_2$, $SnCl_2 \cdot 2H_2O$, $NiBF_4$ in wet acetonitile, most preferably $ZnBr_2$ in methylene chloride; by transacetalization reaction with ketones in the presence of catalysts preferably with acetone in the presence of iodine; by pyridinium p-toluenesulfonate in wet acetone; DDQ; Montmorillonite K10; $CBr_4/MeCN/H_2O$; $Me_3SiI$.

The hydrated form of formula V' or V may be used for the Wittig reaction without further purification by dissolution in an appropriate solvent (toluene or dichloromethane) where dehydration to the compound of formula IV' or IV occurs. In the specific embodiment related to rosuvastatin, in the subsequent reaction step, (2S,4R)-4-(tert-butyldimethylsilyloxy)-6-oxo-tetrahydro-2H-pyran-2-carbaldehyde (IV'), or IV if another protecting group is used, can be reacted under the conditions of a Wittig coupling (in the presence of a base) with a ((4-(4-fluorophenyl)-6-isopropyl-2-(N-methylmethylsulfonamido)pyrimidin-5-yl)methyl)triphenyl-phosphonium halide or any other ((4-(4-fluorophenyl)-6-isopropyl-2-(N-methylmethylsulfon-amido)pyrimidin-5-yl)methyl) phosphonium salt or alternatively di-i-propyl({4-(4-fluorophenyl)-6-isopropyl-2-[methyl(methylsulfonyl)amino]-5-pyrimidinyl}methylphosphonate or any other ({4-(4-fluorophenyl)-6-isopropyl-2-[methyl(methylsulfonyl)amino]-5-pyrimidinyl}methylphosphonate ester to give N-(5-((E)-2-((2S,4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methylmethanesulfonamide (VII'), or an analogue VII if another protecting group is used. As a base, lithium hexamethyldisilazane (LiHMDS), potassium hexamethyldisilazane (KHMDS), sodium hexamethyldisilazane (NaHMDS), lithium diisopropylamide (LDA), sodium hydride, butyllithium or Grignard reagents, preferably sodium hexamethyldisilazane may be used. When the source of IV' is the hydrate thereof form V' or a mixture of IV' and the hydrate form V' thereof, which is dissolved in ethers selected from THF, $Et_2O$, i-$Pr_2O$, $^tBuMeO$; hydrocarbons selected from: pentane, hexane, cyclohexane, methylcyclohexane, heptane; aromatic hydrocarbons selected from toluene or the chlorinated derivatives thereof; chlorinated hydrocarbons selected from: chloroform and dichloromethane or in mixtures of those solvents, the water released from the hydrate should be removed prior to the addition to the formed ylide solution. The preferred solvents for the reaction are anhydrous toluene and dichloromethane. The reaction can be performed at temperatures between −80° C. and 90° C. preferably at 0 to 90° C., more preferably at 80-90° C is accomplished in 1-12 hours. Isolation of the crude product with extraction can be performed with AcOEt, ethers or alkanes as above. Preferably with $^tBuMeO$.

The protecting group may be removed and the lactone opened to produce a rosuvastatin free acid or a salt thereof, optionally an amine, which may be converted to hemicalcium salt. The deprotection can be performed at temperatures between 0° C. to 80° C. Preferably at 20 or 40° C. in a suitable solvent, preferably a solvent selected from alcohols, acetic acid, THF, acetonitrile, methyltetrahydrofuran, dioxane, $CH_2Cl_2$, more preferably in alcohols and a mixture of THF/AcOH. The usual deprotecting reagents may be used, such as tetra-n-butylammonium fluoride, ammonium fluoride, AcCl, $FeCl_3$, $TMSCl/HF.2H_2O$, chloroethyichloroformate (CEC), $Ph_3PCH_2COMeBr$. The opening of the lactone preferably takes place in a 4:1 to 2:1 mixture of THF/$H_2O$ as well as in pure THF at temperatures between 20° C. to 60° C. with a suitable alkali such as NaOH, KOH, ammonia or amines. The hydrolysis is accomplished in 30 minutes (at 60° C.) to 2 hours (at 20° C.). After the hydrolysis step, evaporation of THF can be conducted at temperatures between 10° C. to 50° C. under the reduced pressure, and conversion to the calcium salt, preferably by the addition of $Ca(OAc)_2.xH_2O$, which can be added in one portion or dropwise in 5 to 60 minutes, can be performed at temperatures between 0° C. to 40° C. After the addition of $Ca(OAc)_2.xH_2O$, the resulting suspension can be stirred at temperatures between 0° C. to 40° C. from 30 minutes to 2 hours. To produce other statins, (2S, 4R)-4-(tert-butyl-dimethylsilyloxy)-6-oxo-tetrahydro-2H-pyran-2-carbaldehyde (IV') (or the compound of the general formula IV) should be reacted under analogous conditions of a Wittig coupling with an appropriate reagent followed by hydrogenation when needed.

The standard compound of formula I' was prepared by this chemical synthesis in order to confirm the structure of the enzymatic product. Enzymatically prepared compound of formula I' is chemically equivalent to the compound of formula prepared by the chemical synthesis.

Compounds of formula I'

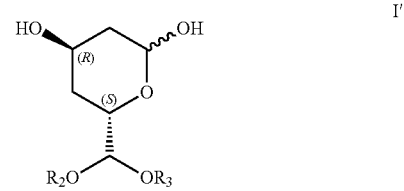

wherein $R_2$ and $R_3$ are independently selected from $C_1$-$C_4$-alkyl, or together form a cyclic structure of formula $(CH_2)_n$ wherein n is from 2 to 6, can be prepared from (4R,6S)-4-(protected)-6-(iodomethyl)-tetrahydropyran-2-one, such as (4R,6S)-4-(tert-butyldimethylsilyloxy)-6-(iodomethyl)-tetrahydropyran-2-one (*J. Chem. Soc., Perkin Trans.* 1 (1991) 133-140) by an acetate substitution, subsequent reaction with $[t-Bu_2SnOH(Cl)]_2$ and the subsequent oxidation with Dess-Martin periodinane (DMP) followed by the reaction with trialkyl ortoformate and reduction with di-s-butylaluminium hydride yielding (4R, 6S)-4-(protected)-6-(dialkoxymethyl)tetrahydro-2H-pyran-2-ol, from which the protecting group is removed with tetra-n-butylammonium fluoride. This synthetic route for the compound of the formula I' is shown in the following scheme:

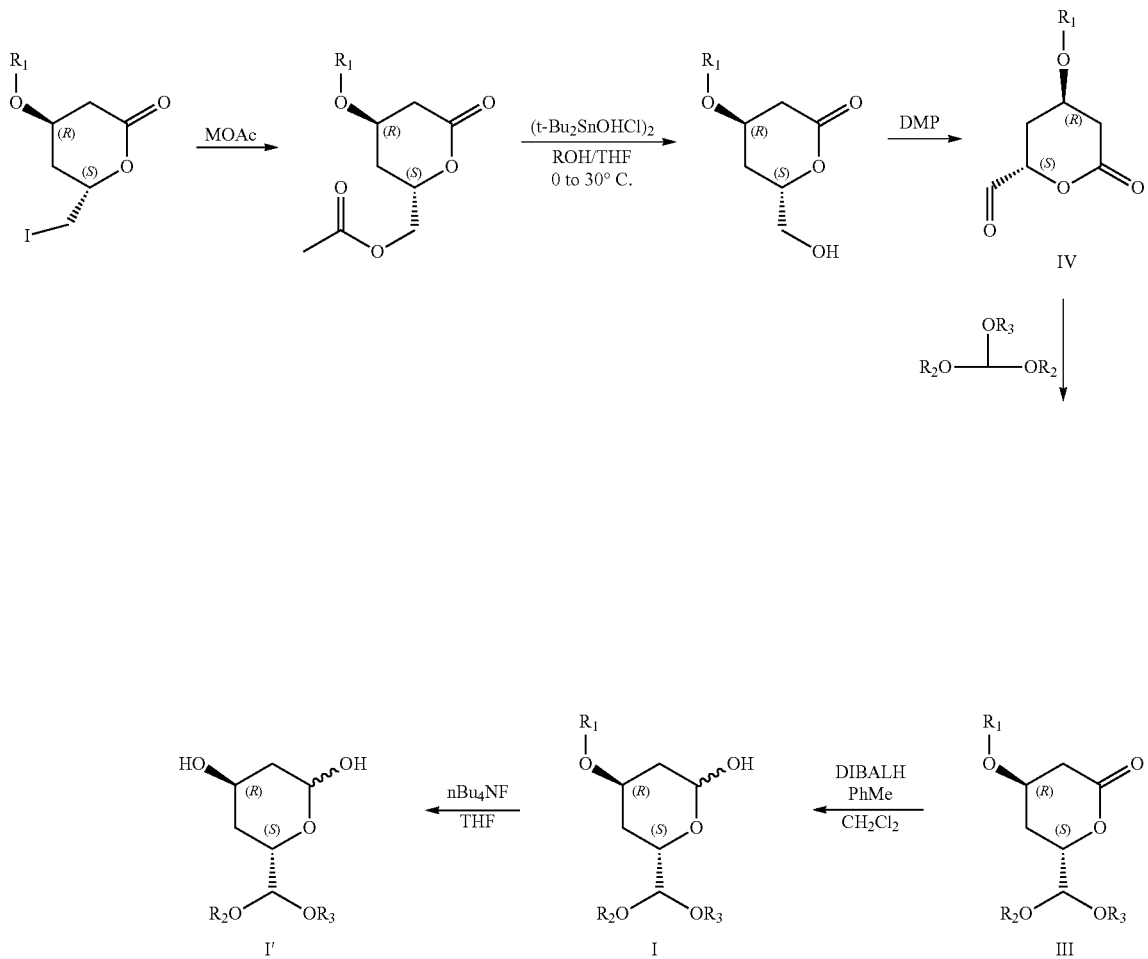

In another embodiment, compound I" may be prepared as outlined on the scheme below starting from dehydroacetic acid P1 which is hydrolysed with 90% sulphuric acid at 130° C., further oxidizing the obtained pyrone P2 by selenium dioxide in diglyme to give a formyl substituted pyrone P3. The aldehyde is further transformed to the corresponding dimethyl acetal P4 by the reaction with methanol in the presence of gaseous hydrogene chloride, then the pyrone ring is reduced by hydrogenation in a two step process first by using 10% palladium on carbon to obtain a dihydro-derivative P5 and then Raney-nickel to obtain a mixture of fully saturated diastereoisomers of the structure P6. The mixture is resolved by transesterification with vinyl acetate in tetrahydrofuran in the presence of a lipase at 40° C. in which the desired 4(R)-6(S) isomer is not acetylated. Finally after removing the lipase by filtration and the solvent by evaporation, the 4(R)-6(S) isomer which is not acetylated is isolated from other acetylated diastereoisomers by column chromatography on silica gel by using ethyl acetate/dichloromethane mixtures. The obtained 6(S)-dimethoxy-4(R)-hydroxytetrahydropyrane-2-one II' is reduced by diisobutylaluminium hydride to obtain I'.

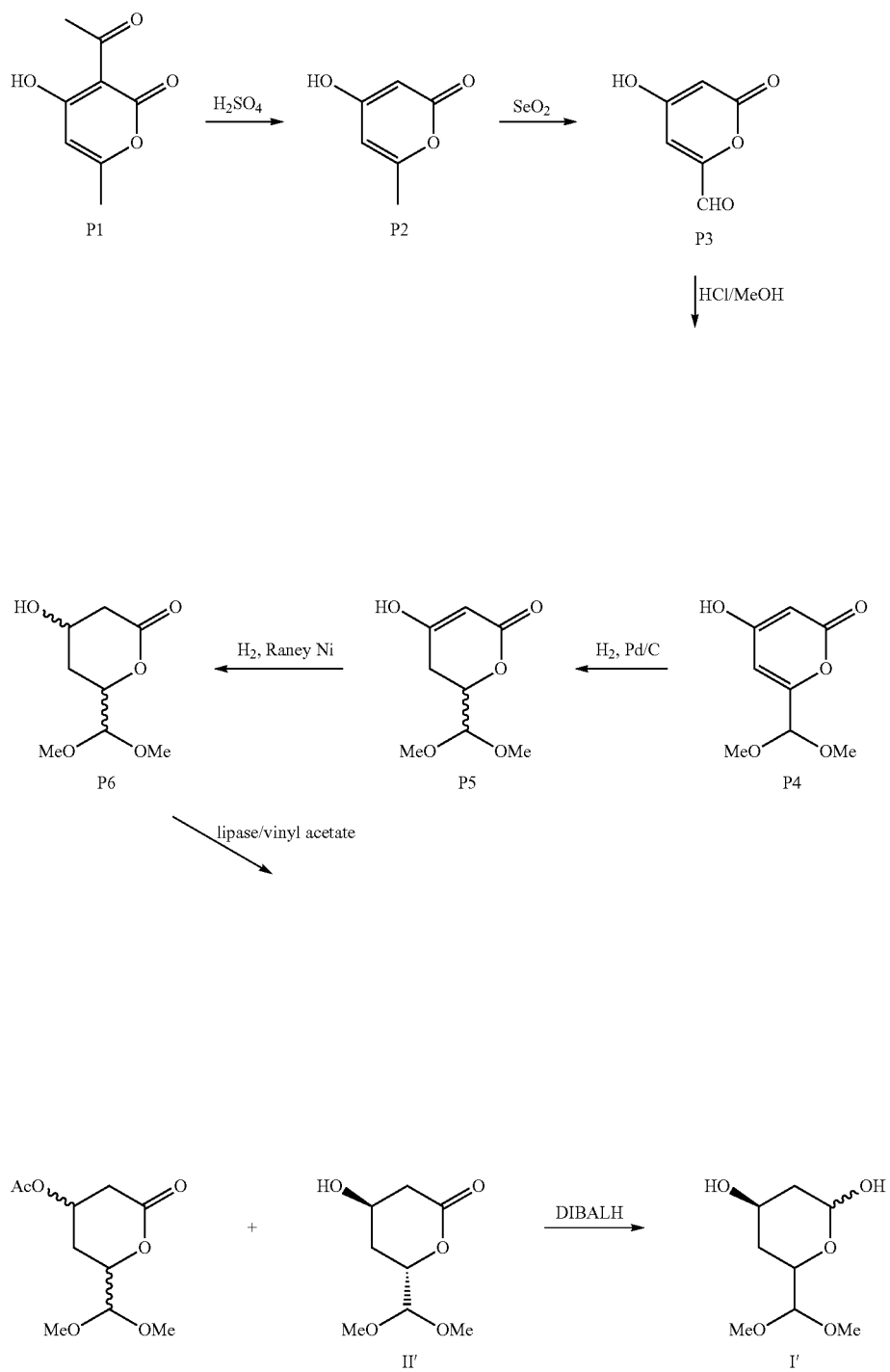

In yet another embodiment, the invention provides an enzymatic process using a substrate of the formula X and acetaldehyde to form the corresponding lactole I' in an aldolase catalysed aldol condensation reaction as shown in the following scheme:

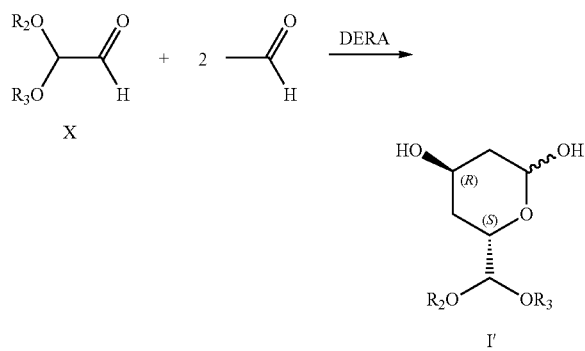

wherein $R_2$ and $R_3$ are independently selected from $C_1$-$C_4$-alkyl, or together form an optionally substituted cyclic structure of formula $(CH_2)_n$ where n is from 2 to 6. Structure I' according to the present invention has a strictly defined stereoisomery at the positions 4 and 6, while other chiral centers may be present in both possibilities forming mixtures of epimers. The changeable chiral centers are not essential for the synthesis of the final product of the invention as the chirality of those carbon atoms is lost during the synthetic procedure.

The term "aldolase-catalyzed aldol condensation conditions" as used herein refers to any aldol condensation conditions known in the art that can be catalyzed by an aldolase, as described herein. In particular, the aldolase-catalysed aldol condensation conditions are such that they allow forming and accumulation of the desired product. These conditions include in one aspect that the aldolase is an active enzyme provided at sufficient load to be able to perform the sequential condensation, in another aspect that the substrate and acetaldehyde are present in the reaction in an amount that does not inhibit the activity of the aldolase. Furthermore the conditions include in one aspect that the temperature, pH, the solvent composition, agitation and length of the reaction allow accumulation of the desired product, in another aspect that said conditions do not have detrimental effect on the product stability. Specifically those conditions are defined by values disclosed in the examples.

Aldolase activity towards the above substrate of the formula X means that the specified enzyme is either purified and/or isolated, or immobilized or within a living cell, or comprised within an inactivated whole cell, or comprised in a homogenized cell material, or in a cell free extract, which will catalyze the above reaction of the substrate X with acetaldehyde to form the corresponding lactol compound of the formula I'.

The term "conditions sufficient to produce statin (in particular rosuvastatin) or a pharmaceutically acceptable salt thereof" as used herein refers to those means described in the art, including those means described herein.

The term an "organism over expressing biologically active form of an aldolase" as used herein refers to any organism having the aldolase expression under control of a strong promoter, and wherein the aldolase is expressed at high levels (compared to w.t. expression control) and is accumulated intracellularly or extracellularly. The process of making such an organism is well known to a person skilled in the art. The present invention provides an example of making such an organism.

An aldolase for use in the present invention may be any compound that has aldolase activity towards the above substrate of formula X. In one embodiment of the invention, the aldolase is a 2-deoxyribose-5-phosphate aldolase (DERA). Examples of a suitable DERA—aldolase include, but are not limited to: DERA 01, DERA 02, DERA 03, DERA 04, DERA 05, DERA 06, DERA 07, DERA 08, DERA 09, DERA 10, DERA 11, DERA 12, DERA 13, DERA 14, DERA 15, DERA 16, DERA 17, DERA 18, DERA 19, DERA 20, DERA 21, DERA 22 and DERA 23 which are identified by their nucleotide sequences or respective codon optimized nucleotide sequences or amino acid sequences set forth in the sequence listings.

In general, any of the DERA aldolases known in the art may be used for the reaction regardless of their sequence identity to the above listed DERA aldolases. The invention provides examples of performing said reactions successfully with two different aldolases having only 30.1% identity. The yields of the reaction however may depend on each aldolase substrate specificity and inhibitory effects of the substrates on each aldolase.

DERA 01 is an aldolase having a nucleotide sequence of SEQ ID NO: 1 or an amino acid sequence of SEQ ID NO: 2; DERA 01 (E. Coli) is commercially available from Sigma Aldrich, St. Louis, Mo., USA, under the catalog number 91252.

DERA 02 is an aldolase having a nucleotide sequence of SEQ ID NO: 3 or SEQ ID NO: 4 or an amino acid sequence of SEQ ID NO: 5; DERA 02 is described in William A. Greenberg, et al., PNAS (2004), Vol. 101, No. 16, p. 5788.

DERA 03 is an aldolase having a nucleotide sequence of SEQ ID NO: 6 or an amino acid sequence of SEQ ID NO: 7

DERA 04 is an aldolase having a nucleotide sequence of SEQ ID NO: 8 or an amino acid sequence of SEQ ID NO: 9

DERA 05 is an aldolase having a nucleotide sequence of SEQ ID NO: 10 or an amino acid sequence of SEQ ID NO: 11

DERA 06 is an aldolase having a nucleotide sequence of SEQ ID NO: 12 or an amino acid sequence of SEQ ID NO: 13

DERA 07 is an aldolase having a nucleotide sequence of SEQ ID NO: 14 or an amino acid sequence of SEQ ID NO: 15

DERA 08 is an aldolase having a nucleotide sequence of SEQ ID NO: 16 or an amino acid sequence of SEQ ID NO: 17

DERA 09 is an aldolase having a nucleotide sequence of SEQ ID NO: 18 or an amino acid sequence of SEQ ID NO: 19

DERA 10 is an aldolase having a nucleotide sequence of SEQ ID NO: 20 or an amino acid sequence of SEQ ID NO: 21

DERA 11 is an aldolase having a nucleotide sequence of SEQ ID NO: 22 or an amino acid sequence of SEQ ID NO: 23

DERA 12 is an aldolase having a nucleotide sequence of SEQ ID NO: 24 or an amino acid sequence of SEQ ID NO: 25

DERA 13 is an aldolase having a nucleotide sequence of SEQ ID NO: 26 or an amino acid sequence of SEQ ID NO: 27

DERA 14 is an aldolase having a nucleotide sequence of SEQ ID NO: 28 or an amino acid sequence of SEQ ID NO: 29

DERA 15 is an aldolase having a nucleotide sequence of SEQ ID NO: 30 or an amino acid sequence of SEQ ID NO: 31

DERA 16 is an aldolase having a nucleotide sequence of SEQ ID NO: 32 or an amino acid sequence of SEQ ID NO: 33

DERA 17 is an aldolase having a nucleotide sequence of SEQ ID NO: 34 or an amino acid sequence of SEQ ID NO: 35

DERA 18 is an aldolase having a nucleotide sequence of SEQ ID NO: 36 or an amino acid sequence of SEQ ID NO: 37

DERA 19 is an aldolase having a nucleotide sequence of SEQ ID NO: 38 or an amino acid sequence of SEQ ID NO: 39

DERA 20 is an aldolase having a nucleotide sequence of SEQ ID NO: 40 or an amino acid sequence of SEQ ID NO: 41

DERA 21 is an aldolase having a nucleotide sequence of SEQ ID NO: 42 or an amino acid sequence of SEQ ID NO: 43

DERA 22 is an aldolase having a nucleotide sequence of SEQ ID NO: 44 or an amino acid sequence of SEQ ID NO: 45

DERA 23 is an aldolase having a nucleotide sequence of SEQ ID NO: 46 or an amino acid sequence of SEQ ID NO: 47

The aldolase encompases an aldolase having an amino acid sequence identity of at least about 50% thereof; preferably at least 70% thereof, to a aldolase described herein. The amino acid sequence identities are determined by the analysis with a sequence comparison algorithm or by a visual inspection. In one aspect the sequence comparison algorithm is made with AlignX algorithm of Vector NTI 9.0 (InforMax) with settings set to default.

In particular, the invention provides for a process comprising the step of reacting a substrate of formula X with acetaldehyde under aldolase-catalysed aldol condensation conditions to form the corresponding lactol

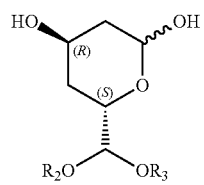

wherein the substrate of formula X

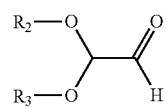

wherein $R_2$ and $R_3$ are independently selected from $C_1$-$C_4$-alkyl, or together form a cyclic structure of formula $(CH_2)_n$ wherein n is from 2 to 6, and subsequent use thereof in the synthesis of statins (in particular rosuvastatin). In this process, in a first embodiment, the aldolase is selected from DERA 01, DERA 06 or DERA 07, or any aldolase having an amino acid sequence identity of at least about 90% to those. In another embodiment, the aldolase is selected from DERA 02 or DERA 15 or DERA 16, or any aldolase having an amino acid sequence identity of at least about 90% to those.

The DERA aldolases described herein can be prepared by any means known in the art, including but not limited to standard protocols for protein expression in recombinant *E. coli* such as described in Sambrook and Russell, Molecular Cloning: A Laboratory Manual, 3'^" Ed., Cold Spring Harbor, N.Y. 2001. Modified versions of known DERA aldolases may be necessary or may result depending on cloning conditions and are encompassed by the present invention.

The DERA aldolases described herein can be used in any biologically active form. In one embodiment, the aldolase is active and can be used in the form of a living whole cell catalyst. In another embodiment, the aldolase is active and can be used in the form of an inactivated whole cell catalyst. In yet another embodiment, the aldolase is active and can be used in the form of a homogenized whole cell catalyst. In one embodiment, the aldolase is active and can be used in the form of a cell free extract. In a further embodiment, the aldolase is active and can be used in the form of a purified enzyme by means of any methods known in the art. In another aspect, the aldolase is active and can be used in the form of an extracelularly expressed protein.

Alternatively, the present invention provides a method of preparing intermediates for the production of statins by using a whole cell catalyst. In one embodiment, the whole cell catalyst is any prokaryotic organism over expressing biologically active form of an aldolase. In a particular embodiment, the whole cell catalyst is Escherichia coli over expressing biologically active form of an aldolase.

Substrates and reaction conditions were chosen to give the optimal activity of an aldolase used to make the intermediates useful for a statin production.

The substrates X are in the first aspect selected according to their inhibitory effects towards the aldolase activity. In particular the acceptor substrates with the least inhibitory effect are suitable for the reaction.

The substrates X are also selected according to their product stability and to the corresponding lactol I' product stability at optimal reaction conditions. In particular the acceptor substrates with the best stability are preferred for the reaction.

The substrates X may be in particular 2,2-dimethoxyethanal (preferred), 2,2-diethoxyethanal; 2,2-dipropoxyethanal; 2,2-dibutoxyethanal; 1,3-dioxolane-2-carbaldehyde; 4-methyl-1,3-dioxolane-2-carbaldehyde; 4-ethyl-1,3-dioxolane-2-carbaldehyde; 4-propyl-1,3-dioxolane-2-carbaldehyde; 4-butyl-1,3-dioxolane-2-carbaldehyde; 4,5-dimethyl-1,3-dioxolane-2-carbaldehyde. Alternatively the substrates may be the structures which according to conditions of the enzymatic reaction lead to compounds generated in situ, like

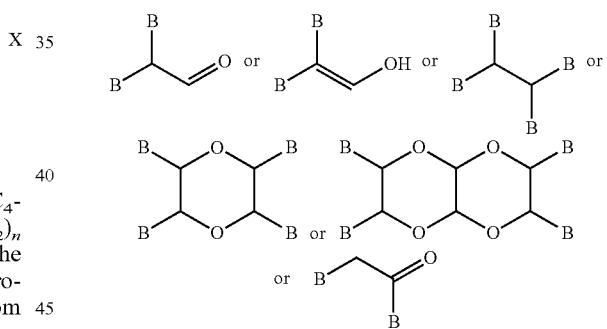

wherein substituents B are the same or different selected from OH, $C_1$-$C_4$-alkoxy, halogen and azido groups.

Generally aldolase will be provided in a suitable vessel or reactor, and the substrate of formula X and acetaldehyde will be added batch-wise or continuously.

Specifically aldolase is prepared in an aqueous solution (particularly in a concentration 0.1 g/L to 3 g/L), optionally in the presence of a salt (in particular NaCl in a concentration from 50 to 500 mM). The aqueous solution may contain organic solvents miscible with water (in particular dimethyl sulfoxide in a concentration from 2 to 15% V/V), and may be buffered to pH 6 to 11. Suitable buffers can be prepared from: acids, bases, salts or mixtures thereof, and any other buffer system known in the art except those possessing a primary, secondary or tertiary amino group. In particular, phosphate buffer, in a concentration 10 to 500 mM can be used. The aqueous solution can also be prepared by adding the aldolase to water and maintaining the pH-value during the reaction by means of an automated addition of inorganic acids, bases, salts or mixtures thereof.

In the process aspect, the substrate of formula X may be added to the reaction mixture continuously or alternatively the substrate of formula X may be added to the reaction mixture in one batch or more batches. In one aspect, the total amount of substrates added to the mixture is such that the total amount of the substrate (I) added would be from about 20 mmol per liter of the reaction mixture to about 2 mol per liter of the reaction mixture, in particular from about 100 mmol per liter of the reaction mixture to about 1.5 mmol per liter of the reaction mixture, more particular from about 200 mmol per liter of the reaction mixture to about 700 mmol per liter of the reaction mixture. Acetaldehyde may be added by several means. In one aspect, acetaldehyde is added to the reaction mixture in one batch or more batches or alternatively continuously. Acetaldehyde may be premixed with the substrate of formula X and added to the reaction mixture. The total amount of acetaldehyde added to the reaction mixture is from about 0.1 to about 4 molar equivalents to the total amount of the acceptor substrate, in particular from about 2 to about 2.5 molar equivalents.

Alternatively aldolase may be added to the reaction mixture containing a solvent and at least one of the substrate of formula X or acetaldehyde. The substrate X or acetaldehyde which is not comprised in the provided reaction mixture may be added together with aldolase or after the addition of aldolase.

In one aspect of the invention, the pH-value used for the aldolase-catalyzed reaction is from about 5 to about 12. In one embodiment, the pH used for aldolase-catalyzed reaction is from about 6 to about 10. In another embodiment, the pH-value used for aldolase-catalyzed reaction is from about 7 to about 9. Specifically the pH-value will be maintained by a suitable buffer in a range from 7.2 to 8.5.

Some commonly used buffers can lower the yield of the aforementioned aldolase-catalysed reaction by limiting the availability of aldolase-condensation intermediates, particularly first condensation reaction products as they may undergo a chemical reaction with a buffer. We discovered that bis-tris propane reacts with said intermediates ((S)-3-hydroxy-4,4-dimethoxybutanal) giving (S,Z)-2-(3-((1,3-dihydroxy-2-hydroxymethyl)propan-2-yl)(3-hydroxy-4,4-dimethoxybut-1-enyl)amino)propylamino)-2-(hydroxymethyl)propan-1,3-diol. Other buffers that may react similarly are bis-tris, tricin, tris, bicin or any other buffer having a primary, secondary or tertiary amino group. Thus suitable buffers for adjusting pH, if this adjustment is needed, are made with acids, bases, salts or mixtures thereof, in particular phosphoric acid and sodium hydroxide. In a particularly preferred embodiment, the buffer is a phosphate buffer.

In one aspect according to the invention, the temperature used for the aldolase-catalyzed reaction is from about 20 to about 70° C. In one embodiment, the temperature used for aldolase-catalyzed reaction is from about 25 to about 60° C. In another embodiment, the temperature used for aldolase-catalyzed reaction is from about 30 to about 50° C.

The reaction is industrially suitable, as it proceeds to completion within few hours.

The effects of reaction conditions, notably pH, temperature and reaction time are surprising, especially in view of the teaching of J. Am. Chem. Soc., 117, 29, (1995) p. 7585, where the reaction with 2,2-dimethoxyethanal did not proceed even in 6 days.

After the completion of the reaction, the enzyme is removed from the reaction mixture, for example by the addition of at least about 1 vol. of acetonitrile to 1 vol. of reaction mixture. Alternatively the enzyme is removed by any salting out method known in the art. In one embodiment the salting out is performed with the addition of ammonium sulfate of at least 5% m/V.

The invention also provides a purification method for obtaining pure lactols produced by the aldolase-catalysed aldol condensation reaction. In one aspect, acetonitrile is evaporated from the reaction mixture and the remaining aqueous solution is then lyophilised. In another aspect, the salting-out solution is lyophilised. The powdered remainder is then suspended in MTBE (methyl-t-butylether)/methanol 1:1. The suspension is filtered to remove insoluble salts and the filtrate is loaded to a silicagel column by using MTBE/Methanol 1:1 as the mobile phase.

In a particular embodiment, the invention provides for the reaction of 2,2-dimethoxyethanal with acetaldehyde under aldolase-catalysed aldol condensation to form (4R,6S)-6-dimethoxymethyl)-tetrahydro-2H-pyran-2,4-diol wherein the used aldolase is DERA 01, DERA 02 or DERA 08 in an appropriate solvent (in particular an aqueous solvent, which may be water in a mixture with a water soluble organic solvent) in a pH range from 6 to 11, in particular from 7 to 9 (adjusted if needed with acids, bases, salts or mixtures thereof in particular with phosphoric acid and sodium hydroxide). The reaction proceeds at a temperature around 35-40° C. and the conversion is finished in 1 to 6 hours.

In general, the aldolase used is prepared by methods of protein expression described in Sambrook et al. (1989) Molecular cloning: A laboratory Manual $2^{nd}$ Edition, New York: Cold Spring Harbor Laboratory Press, Cold Spring Harbor. Gene coding aldolase is cloned into an expression vector and the enzyme is expressed in a suitable expression host.

The reaction yields are calculated relatively to the total amount of the substrate of formula X added to the reaction mixtures and they are determined as the ratio between moles of the isolated product and moles of the substrate of formula X added to the reaction mixture.

The following examples illustrate the process of the present invention and are not intended to limit the scope of the invention.

EXAMPLE 1

Synthesis of the Standard

1. Step: Preparation of ((2S,4R)-4-(tert-butyldimethylsilyloxy)-6-oxo-tetrahydro-2H-pyran-2-yl)methyl acetate To a solution of (4R,6S)-4-(tert-butyldimethylsilyloxy)-6-(iodomethyl)-tetrahydropyran-2-one (40.00 g, 108.0 mmol) in AcOH (660 mL), AgOAc (20.03 g, 118.8 mmol) is added. The resultant mixture is then heated at 125° C. for 6 hours. The reaction mixture is filtered through diatomite filter medium (Celite®). The obtained filtrate is evaporated to afford the residue. To this residue, EtOAc (500 mL) and water (600 mL) are added. The organic layer is separated and the aqueous layer is washed again with EtOAc (5×150 mL). The combined organic layers are washed with water (4×300 mL), brine (5×300 mL) and dried over anhydrous $MgSO_4$, filtered and concentrated under the reduced pressure to afford 30.28 g (92.6%) of ((2S,4R)-4-(tert-butyldimethylsilyloxy)-6-oxo-tetrahydro-2H-pyran-2-yl)methyl acetate as yellow oil (HPLC purity 98%).

$^1$H-NMR (300 MHz, $CDCl_3$) δ: 4.93 (m, 1H), 4.37 (m, 1H), 4.30 (dd, J=12 Hz, J=3 Hz, 1H), 4.21 (dd, J=12 Hz, J=5

Hz, 1H), 2.62 (d, J=4 Hz, 2H), 2.11 (s, 3H), 1.84-1.80 (m, 2H), 0.89 (s, 9H), 0.09, 0.09 (2s, 6H).
$^{13}$C-NMR (75 MHz, CDCl$_3$) δ: 170.4, 169.1, 73.3, 65.5, 63.0, 38.9, 32.2, 20.5, 17.7, −5.1, −5.2.

2. Step: Preparation of (4R,6S)-4-(tert-butyldimethylsilyloxy)-6-(hydroxymethyl)-tetrahydropyran-2-one ((2S,4R)-4-(tert-Butyldimethylsilyloxy)-6-oxo-tetrahydro-2H-pyran-2-yl)methyl acetate (8.36 g, 27.64 mmol) and [$^t$Bu$_2$SnOH(Cl)]$_2$ (1.577 g, 2.764 mmol) are dissolved in MeOH/THF mixture (280 mL). The reaction mixture is stirred at 23-25° C. for 27 h. After the solvent is removed under reduced pressure, the remained residue is purified by silica gel chromatography (elution with $^t$BuMeO/hexane mixture) to afford a crude product as white solid (5.59 g, 78%). Recrystallization from n-hexane affords (3.90 g, 54%) of (4R,6S)-4-(tert-butyldimethylsilyloxy)-6-(hydroxymethyl)-tetrahydro-pyran-2-one as white needles. M.p.=102° C. (DSC peak).
$^1$H-NMR (300 MHz, CDCl$_3$) δ: 4.80 (m, 1H), 4.38 (m, 1H), 3.91 (dd, J=12 Hz, J=3 Hz, 1H), 3.66 (dd, J=12 Hz, J=5 Hz,1H), 2.60 (d, J=4 Hz, 2H), 2.31 (bs, 1H), 1.97-1.75 (m, 2H), 0.88 (s, 9H), 0.09, 0.08 (2s, 6H).
$^{13}$C-NMR (75 MHz, CDCl$_3$) δ: 170.1, 76.8, 64.7, 63.4, 39.2, 31.9, 25.6, 17.9, −4.9, −5.0.

3. Step: Preparation of (4R,6S)-4-(tert-butyldimethylsilyloxy)-6-(dihydroxymethyl)tetrahydro-2H-pyran-2-one (V')

A mixture of (4R,6S)-4-(tert-butyldimethylsilyloxy)-6-(hydroxymethyl)-tetrahydropyran-2-one (150 mg, 0.58 mmol) and Dess-Martin periodinane (380 mg, 0.86 mmol) in CH$_2$Cl$_2$ (15 mL) is stirred at ambient temperature for 3 hours. The mixture is diluted with $^t$BuMeO (20 mL), washed with saturated Na$_2$S$_2$O$_3$ solution, saturated NaHCO$_3$ solution, dried (MgSO$_4$) and concentrated to give 139 mg (87%) of (4R,6S)-4-(tert-butyldimethylsilyloxy)-6-(dihydroxymethyl)tetrahydro-2H-pyran-2-one as white powder which is used in the next step without further purification.
$^1$H-NMR (300 MHz, THF-d$_8$) δ: 5.27 (d, J=6 Hz, 1H, OH), 5.19 (d, J=6Hz, 1H, OH), 4.90-4.85 (m, 1H), 4.44-4.38 (m, 2H), 2.58 (dd, J=17 Hz, J=4 Hz, 1H), 2.44-2.36 (m, 1H), 1.92-1.87 (m, 2H), 0.91 (s, 9H), 0.10 (s, 6H).
$^{13}$C-NMR (75 MHz, THF-d$_8$) δ: 168.7, 91.7, 79.0, 65.1, 40.3, 31.0, 26.2, 18.7, −4.8, −4.8.

4. Step: Preparation of (4R,6S)-4-(tert-butyldimethylsilyloxy)-6-(dimethoxymethyl)tetrahydro-2H-pyran-2-one (III')

To a solution of 1.0 g of (4R,6S)-4-(tert-butyldimethylsilyloxy)-6-(dihydroxymethyl)-tetrahydro-pyran-2-one (V') in 100 mL of dichloromethane, 50 mg of toluenesulfonic acid and 4.5 mL of trimethyl orthoformate are added. After 2 hours of stirring at 25° C., 0.2 g of NaHCO$_3$ is added and dichloromethane is distilled off. The residue is flash chromatographed (MTBE/hexane 1/1) and the solvents are distilled off to get the title compound.
Yield: 0.70 g of yellow, crystalline powder.
$^1$H-NMR (300 MHz, CDCl$_3$) δ: 0.08 (s), 0.88 (s), 1.8-1.9 (m), 2.5-2.7 (m), 3.44 (s), 3.45 (s), 4.36 (t), 4.42 (d), 4.73 (m).
$^{13}$C-NMR (75 MHz, CDCl$_3$) δ: −5.0, 17.9, 25.6, 26.9, 29.7, 39.5, 55.8, 56.8, 63.3, 75.7, 105.1, 169.5.

5. Step: Preparation of (4R,6S)-4-(tert-butyldimethylsilyloxy)-6-(dimethoxymethyl)-tetrahydro-2H-pyran-2-ol (I')

A solution of 0.6 g of (4R,6S)-4-(tert-butyldimethylsilyloxy)-6-(dimethoxymethyl)-tetrahydropyran-2-one (III') in 36 mL of dichloromethane is cooled to −78° C. after 2 mL of DIBALH (25% in toluene) are added over 10 minutes. After 1 hour of stirring at −78° C., 0.9 g of Rochelle salt in 60 mL of water are added, phases are separated and dichloromethane is distilled off. The residue is flash chromatographed (MTBE/hexane 1/1) and the solvents are distilled off to get the title compound.
Yield: 0.47 g of yellow oil.
Mixture of α and β anomers:
$^1$H-NMR (300 MHz, CDCl$_3$) δ: 0.10 (s), 0.86 (s), 0.89 (s), 1.4-1.9 (m), 3.35 (s), 3.42 (s), 4.02 (m), 4.2-4.4 (m), 5.13 (d), 5.23 (d), 5.51 (d).
$^{13}$C-NMR (75 MHz, CDCl$_3$) δ: −5.6, −5.2, 17.7, 17.8, 25.5, 32.1, 33.2, 36.0, 40.1, 53.8, 54.2, 54.6, 55.0, 92.7, 92.8, 105.5, 105.6.

6. Step: Preparation of the Standard, (4R,6S)-6-(dimethoxymethyl)-tetrahydro-2H-pyran-2,4-diol (I")

To a solution of 0.47 g of (4R,6S)-4-(tert-butyldimethylsilyloxy)-6-(dimethoxymethyl)-tetrahydro-2H-pyran-2-ol (I') in 14 mL of tetrahydrofurane, tetra-n-butylammonium fluoride in 14 mL of THF is added. After 15 minutes of stirring at 25° C., the THF is distilled off. The residue is flash chromatographed (methanol). After methanol is distilled off, the title compound is obtained as an oil.
Yield: 0.18 g of yellow oil.
Mixture of α and β anomers:
$^1$H-NMR : (300 MHz, CDCl$_3$) δ: 1.4-2.1 (m), 3.44 (s), 3.45 (s), 4.05 (m), 4.20-4.50 (m), 5.20 (dd), 5.38 (d).
$^{13}$C-NMR : (300 MHz, CDCl$_3$) δ: 32.8, 35.0, 54.4, 54.5, 54.9, 55.0, 62.8, 64.5, 64.9, 70.4, 92.5, 92.9, 105.4, 105.7.

EXAMPLE 2

Example 2.1

Preparation of Aldolase

*Escherichia coli* gene deoC has been amplified by using oligonucleotide primers CGGGATCCACTGATCTGAAAGCAAGCAGCC (SEQ ID NO: 48) and GCAAGCTTGCTGCTGGCGCTCTTACC (SEQ ID NO: 49) in a PCR reaction using isolated genome DNA from *E. coli* K-12 strain. The product was cleaved with restriction endonucleases BamHI and HindIII and the resulting fragment has been separated on agarose gel electrophoresis and purified. An expression vector pQE30 (Qiagene inc., Valencia, Calif., USA) has been cleaved by using the same aforementioned restriction endonucleases and purified. The fragments have been assembled in a T4 ligase reaction. Competent *Escherichia coli* DH5alpha cells were transformed with the above mentioned ligation reaction. Ampicilin resistance colonies were cultured and plasmid DNA has been isolated. The resulting construct has been designated pQE30DeraC and sequenced for conformation of the gene sequence. Aldolase expressing organism has been prepared by transforming competent *Escherichia coli* TOP10 F' strain (Invitrogen corp., Carlsbad, Calif., USA) with vector pQE30DeraC. The methods used for the process are described in Sambrook, et al. (1989) Molecular cloning: A laboratory Manual 2$^{nd}$ Edition, New York: Cold Spring Harbor Laboratory Press, Cold Spring Harbor and are well known to a person skilled in the art.

Terrific Broth media (150 mL, 12 g/L bacto tryptone, 24 g/L bacto yeast extract, 4 mL/L glycerol, 2.31 g/L $KH_2PO_4$, 12.54 g/L $K_2HPO_4$) supplemented with ampicillin (100 μg/mL) was inoculated with 3 mL of TOP10 F' PQE30DeraC overnight culture. Cells were grown (37° C., 250 rpm) until $OD_{600}$ reached approx. 0.8. Protein expression was induced with IPTG (1 mM final concentration) and cells were left in the same growing conditions for additional 4 h. The cell pellet was harvested by centrifugation (10 min, 6000 g, 4° C).The pellet was resuspended in phosphate buffer (9 mL, 50 mM $NaH_2PO_4$, pH 8.0, 300 mM NaCl) giving whole cell catalyst. Alternatively the pellet was resuspended in lytic buffer (9 mL, 50 mM $NaH_2PO_4$, pH 8.0, 300 mM NaCl, 2 mM DTT). Cells were sonified (3×15 s) by using Branson digital sonifier and cell debris was removed by sedimentation (10 min, 20 000 g, 4° C.). Clear aqueous solution of DERA 01 was thus obtained.

Example 2.2

Aldolase Catalyzed Aldol Condensation Conditions

Example 2.2.1

Preparation of (4R,6S)-6-(dimethoxymethyl)tetrahydro-2H-pyran-2,4-diol [I"]

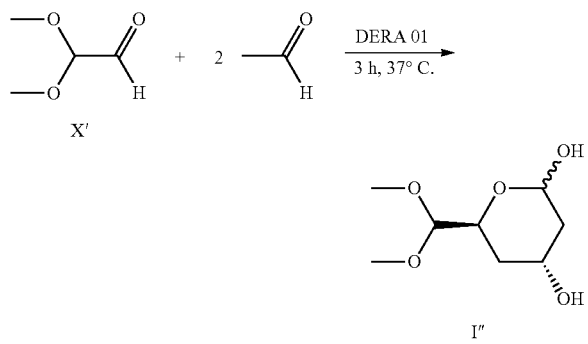

To a solution of phosphate buffer (700 mL, 50 mM $NaH_2PO_4$, pH 8.0, 300 mM NaCl) and 2,2-dimethoxyethanal X' (100 mL, 0.5 M in phosphate buffer, as described above), an aqueous solution of DERA 01 (100 ml, prepared according to Example 2.1) and a solution of acetaldehyde (Fluka, 100 mL, 1.0 M in phosphate buffer as described above) was added. The mixture was stirred for 3 h at 37° C. and pH was regulated at 8.0 with NaOH. The conversion of the reaction was monitored by gas chromatography (GC). After 3 h, the proteins in the reaction mixture (1 L) were precipitated with acetonitrile (4 L) and the solution was filtered by using celite and glass filter. The acetonitrile was evaporated and residual water was removed with lyophilization to give the crude lactol I" (18 g), which was directly solubilized, filtered and submitted to a silica-gel column (methanol/t-butyl methyl ether 1:1). Fractions were collected and analyzed by thin-layer silica-gel chromatography (diisopropyl ether/acetonitrile 2:1). The solvent from the fraction with the product I" was evaporated and the dried product (154 mg, 1.6% yield) was analyzed by $^1$H- and $^{13}$C-NMR. Data for the major anomer:

$^1$H-NMR (300 MHz, $CDCl_3$): δ=1.4-1.9 (m), 3.42 (s), 4.15-4.35 (m), 5.25 (d).

$^{13}$C-NMR (300 MHz, $CDCl_3$): δ=32.8, 35.0, 54.5, 54.9, 62.8, 64.5, 92.9, 105.4, 105.7.

Example 2.2.2

Preparation of (4R,6S)-6-(dimethoxymethyl)tetrahydro-2H-pyran-2,4-diol (I")

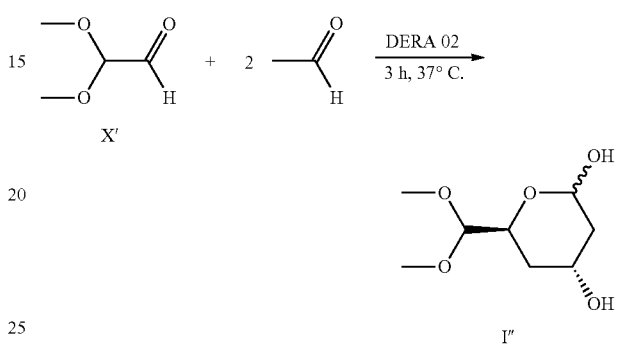

To a solution of phosphate buffer (700 mL, 50 mM $NaH_2PO_4$, pH 8.0, 300 mM NaCl) and 2,2-dimethoxyethanal (100 mL, 0.5 M in phosphate buffer, as described above), an aqueous solution of DERA 02 (100 ml, prepared by an analogue method to the one described in Example 2.1) and a solution of acetaldehyde (Fluka, 100 mL, 1.0 M in phosphate buffer, as described above) was added. The mixture was stirred for 3 h at 37° C. and the pH was kept at 8.0. The conversion of the reaction was monitored by gas chromatography (GC). After 3 h, the proteins in the reaction mixture (1 L) were precipitated with acetonitrile (4 L) and the solution was filtered by using celite and glass filter. Acetonitrile was evaporated and residual water was removed with lyophilization to give the crude lactol I" (22 g), which was directly solubilized, filtered and submitted to a silica-gel column (methanol/t-butyl methyl ether 1:1). Fractions were collected and analyzed by thin-layer silica-gel chromatography (diisopropyl ether/acetonitrile 2:1). The solvent from the fraction with the product I" was evaporated and the dried product (2.8 g, 29% yield) was analyzed by $^1$H- and $^{13}$C-NMR. Data for the major anomer:

$^1$H-NMR (300 MHz, $CDCl_3$): δ=1.4-1.9 (m), 3.42 (s), 4.15-4.35 (m), 5.25 (d).

$^{13}$C-NMR (300 MHz, $CDCl_3$): δ=32.8, 35.0, 54.5, 54.9, 62.8, 64.5, 92.9, 105.4, 105.7.

Example 2.2.3

Preparation of (4R,6S)-6-(dimethoxymethyl)tetrahydro-2H-pyran-2,4-diol (I")

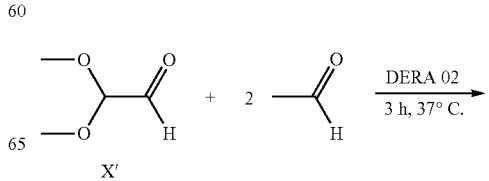

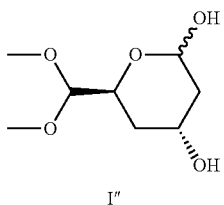

I″

To a solution of phosphate buffer (700 mL, 50 mM NaH$_2$PO$_4$, pH 8.0, 300 mM NaCl) and 2,2-dimethoxyethanal (100 mL, 1.0M in phosphate buffer, as described above), a whole cell catalyst with DERA 02 (100 ml, prepared by an analogue method to the one described in Example 2.1) and a solution of acetaldehyde (Fluka, 100 mL, 2.0 M in phosphate buffer, as described above) was added. The mixture was stirred for 3 h at 37° C. and pH was kept at 8.0. The conversion of the reaction was monitored by gas chromatography (GC). After 3 h, the cells were removed by sedimentation (10 min, 6000 g, 4° C.). Residual water was removed by lyophilization to give the crude lactol I″ (23 g) as an oil, which was directly solubilized, filtered and submitted to a silica-gel column (methanol/t-butyl methyl ether 1:1). Fractions were collected and analyzed by thin-layer silica-gel chromatography (diisopropyl ether/acetonitrile 2:1). The solvent from the fraction with the product I″ was evaporated and the dried product (1.8 g, 9.4% yield) was analyzed by $^1$H- and $^{13}$C-NMR.

$^1$H-NMR (300 MHz, CDCl$_3$): δ=1.4-1.9 (m), 3.42 (s), 4.15-4.35 (m), 5.25 (d).

$^{13}$C-NMR (300 MHz, CDCl$_3$): δ=32.8, 35.0, 54.5, 54.9, 62.8, 64.5, 92.9, 105.4, 105.7.

Example 2.2.4

Preparation of (4R,6S)-6-(dimethoxymethyl)tetrahydro-2H-pyran-2,4-diol (I″)

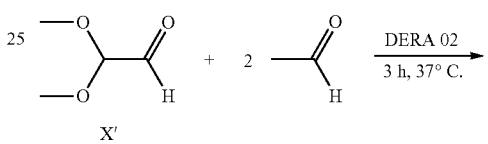

X′

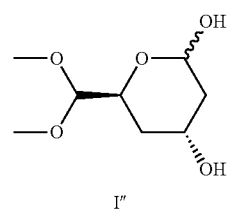

I″

To a solution of phosphate buffer (700 mL, 50 mM NaH$_2$PO$_4$, pH 8.0), an aqueous solution of DERA 02 (100 mL, prepared by an analogue method to the one described in Example 2.1) was added. A solution of 2,2-dimethoxyethanal (Aldrich, 100 mL, 1.0 M in phosphate buffer, as described above) and acetaldehyde (Fluka, 100 mL, 2.0 M in phosphate buffer, as described above) was continuously added separately to the above DERA solution by a programmed pump within 2 h. The mixture was stirred for 3 h at 37° C. and pH was kept at 8.0. The conversion of the reaction was monitored by gas chromatography (GC). After 3 h, the proteins in the reaction mixture (1 L) were precipitated with acetonitrile (4 L) and the solution was filtered by using celite and glass filter. Acetonitrile was evaporated and residual water was removed by lyophilization to give the crude lactol I″ (15 g), which was directly solubilized, filtered and submitted to a silica-gel column (methanol/t-butyl methyl ether 1:1). Fractions were collected and analyzed by thin-layer silica-gel chromatography (diisopropyl ether/acetonitrile 2:1). The solvent from the fraction with the product I″ was evaporated and the dried product (6.2 g, 23.3% yield) was analyzed by $^1$H- and $^{13}$C-NMR $^1$H-NMR (300 MHz, CDCl$_3$): δ=1.4-1.9 (m), 3.42 (s), 4.15-4.35 (m), 5.25 (d).

$^{13}$C-NMR (300 MHz, CDCl$_3$): δ=32.8, 35.0, 54.5, 54.9, 62.8, 64.5, 92.9, 105.4, 105.7.

Example 2.2.5

Preparation of (4R,6S)-6-(dimethoxymethyl)tetrahydro-2H-pyran-2,4-diol (I″)

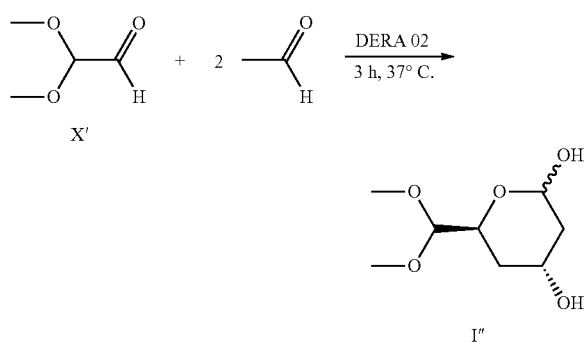

X′

I″

To a solution of phosphate buffer (700 mL, 50 mM NaH$_2$PO$_4$, pH 8.0), an aqueous solution of DERA 02 (100 mL, prepared by an analogue method to the one described in Example 1) and a solution of 2,2-dimethoxyethanal (Aldrich, 100 mL, 4.0 M in phosphate buffer, as described above) was added. A solution of acetaldehyde (Fluka, 100 mL, 8.0 M in phosphate buffer, as described above) was continuously added to the above DERA solution by a programmed pump within 2 h. The mixture was stirred for 3 h at 37° C. and pH was kept at 8.0. The conversion of the reaction was monitored by gas chromatography (GC). After 3 h the proteins in the reaction mixture (1 L) were precipitated with acetonitrile (4 L) and the solution was filtered by using celite and glass filter. Acetonitrile was evaporated and residual water was removed by lyophilization to give the crude lactol I″ (37 g), which was directly solubilized, filtered and submitted to a silica-gel column (methanol/t-butyl methyl ether 1:1). Fractions were collected and analyzed by thin-layer silica-gel chromatography (diisopropyl ether/acetonitrile 2:1). The solvent from the fraction with the product I″ was evaporated and the dried product (9.4 g, 12.2% yield) was analyzed by $^1$H- and $^{13}$C-NMR.

$^1$H-NMR (300 MHz, CDCl$_3$): δ=1.4-1.9 (m), 3.42 (s), 4.15-4.35 (m), 5.25 (d).

$^{13}$C-NMR (300 MHz, CDCl$_3$): δ=32.8, 35.0, 54.5, 54.9, 62.8, 64.5, 92.9, 105.4, 105.7.

Example 2.3

Preparation of Rosuvastatin

To a solution of 1.4 g of (4R,6S)-6-(dimethoxymethyl)-tetrahydro-2H-pyran-2,4-diol (I″) in 100 mL of water is added 2.4 g barium carbonate and 0.5 mL of bromine at 0° C. After 3 hours of stirring at 0-5° C., the product is extracted three times with 300 mL of ethyl acetate. Finally the ethyl acetate is distilled off. To the 0.5 g of thus prepared (4R,6S)-6-(dimethoxymethyl)-4-hydroxy-tetrahydropyran-2-one (II′) in 50 mL of dichloromethane, a 280 mg of imidazole are added at 25° C. and after cooling to 0° C., 400 mg of tert-butyldimethylsilyl chloride are added. The reaction is then stirred for 18 hours and dichloromethane is distilled off. To a solution of 0.40 g of thus obtained (4R,6S)-4-(tert-butyldimethylsilyloxy)-6-(dimethoxymethyl)-tetrahydropyran-2-one (III′) 35 mg of iodine in 12 mL of acetone are added at 25° C. and stirred for 48 hours. In the next step, 200 mg of the obtained (4R,6S)-4-(tert-butyldimethylsilyloxy)-6-(dihydroxymethyl)tetrahydro-2H-pyran-2-one (IV′) are dissolved in toluene and added to a stirred suspension of ((4-(4-fluorophenyl)-6-isopropyl-2-(N-methylmethyl-sulfonamido)pyrimidin-5-yl)methyl)tributylphosphonium 2,2,2-trifluoroacetate (VI′) (504 mg) and sodium hexamethyl disilazane in dry toluene. The protecting group is removed by tetra-n-butylammonium fluoride trihydrate and the obtained compound VIII is converted to the corresponding calcium salt IX by calcium acetate.

Example 2.4

Preparation of (S,Z)-2-(3-((1,3-dihydroxy-2-(hydroxymethyl)propan-2-yl)(3-hydroxy-4,4-dimethoxybut-1-enyl)amino)propylamino)-2-(hydroxymethyl)propane-1,3-diol [1]

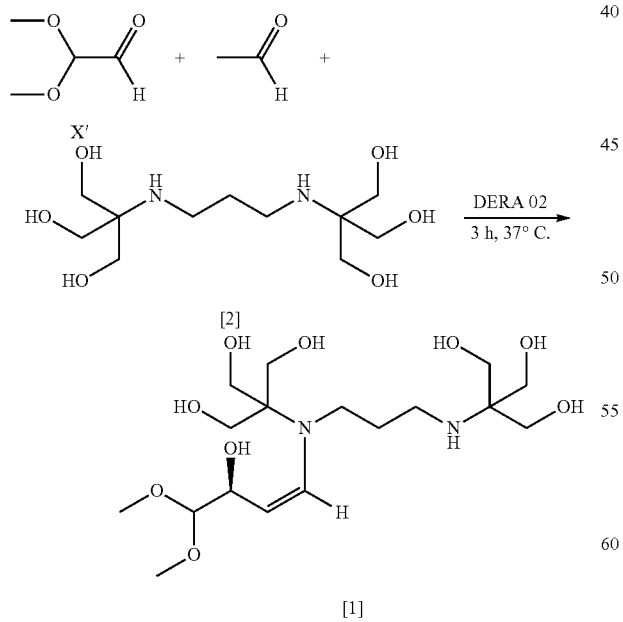

To a solution of bis-tris propane [2] buffer (70 mL, 50 mM bis-tris propane, pH 8.0, 300 mM NaCl) and a solution of 2,2-dimethoxyethanal X′ (10 mL, 0.5 M in bis-tris propane buffer as described above), an aqueous solution of DERA 02 (10 mL, prepared with analogue method to one described in Example 1) and a solution of acetaldehyde (10 mL, 1.0 M in bis-tris propane buffer as described above) was added. The mixture was stirred for 3 h at 37° C. and pH was regulated at 8.0 with NaOH. After 3 h the proteins in the sample (1 mL) from the reaction mixture (100 mL) were precipitated with acetonitrile (9 mL) and the solution was centrifuged. A sample from the supernatant was collected and analyzed directly by HPLC-MS/MS instrument:

HPLC-MS/MS m/z[M+H]⁺ 413.

EXAMPLE 3

Step a): Preparation of (4R,6S)-6-(dimethoxymethyl)-4-hydroxy-tetrahydropyran-2-one (II′)

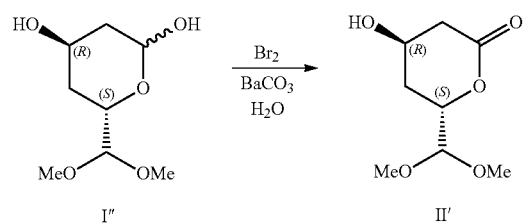

To a solution of 1.4 g of (4R,6S)-6-(dimethoxymethyl)-tetrahydro-2H-pyran-2,4-diol (I′) in 100 mL of water, 2.4 g of barium carbonate and 0.5 mL of bromine at 0° C. are added. After 3 hours of stirring at 0-5° C., the product II′ is extracted three times with 300 mL of ethyl acetate. Finally ethyl acetate is distilled off. The residue is flash chromatographed (DIPE/acetonitrile 2/1). The solvents are distilled off to get the title compound.

Yield: 0.7 g of yellow oil.

¹H-NMR (300 MHz, CDCl₃) δ: 1.8-1.9 (m), 2.5-2.7 (m), 3.40 (s), 3.41 (s), 4.3-4.4 (m), 4.6-4.7 (m).

¹³C-NMR (75 MHz, CDCl₃) δ: 29.3, 38.7, 55.8, 56.9, 62.4, 75.5, 105.0, 169,8.

Step b): Preparation of (4R,6S)-4-(tert-butyldimethylsilyloxy)-6-(dimethoxymethyl)-tetrahydropyran-2-one (III′)

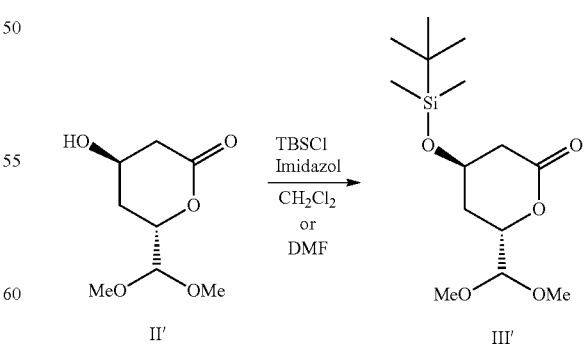

To a solution of 0.5 g of (4R,6S)-6-(dimethoxymethyl)-4-hydroxy-tetrahydropyran-2-one (II′) in 50 mL of dichloromethane, 280 mg of imidazole are added at 25° C. After cooling to 0° C., 400 mg of tert-butyldimethylsilyl chloride are added. The reaction mixture is then stirred for 18 hours and dichloromethane is distilled off. The residue is flash chromatographed (DIPE/acetonitrile=5/1). The solvents are distilled off to get the title compound.

Yield: 0.40 g of yellow, crystalline powder.

$^1$H-NMR (300 MHz, CDCl$_3$) δ: 0.08 (s), 0.88 (s), 1.9 (m), 2.6 (m), 3.44 (s), 3.45 (s), 4.36 (t), 4.42 (d), 4.73 (m).

$^{13}$C-NMR (75 MHz, CDCl$_3$) δ: −5.0, 17.9, 25.6, 26.9, 29.7, 39.5, 55.8, 56.8, 63.3, 75.7, 105.1, 169.5.

Step c): Preparation of (4R,6S)-4-(tert-butyldimethylsilyloxy)-6-(dihydroxymethyl)-tetrahydropyran-2-one (V') and (2S,4R)-4-(tert-butyldimethylsilyloxy)-6-oxo-tetrahydro-2H-pyran-2-carbaldehyde (IV')

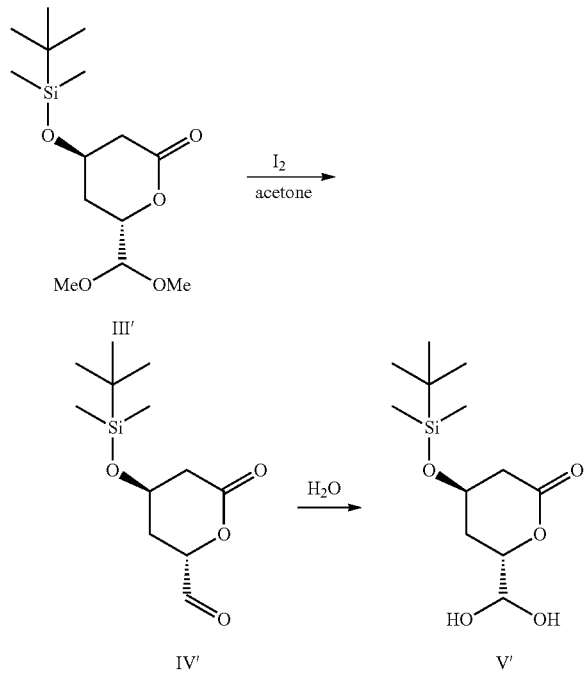

To a solution of 0.40 g of (4R,6S)-4-(tert-butyldimethylsilyloxy)-6-(dimethoxymethyl)-tetrahydropyran-2-one (III') in 12 mL of acetone, 35 mg of iodine are added at 25° C. The reaction mixture is then stirred for 48 hours and acetone is distilled off. Thereafter 25 mL of dichloromethane is added and the reaction mixture is washed with 20 mL of a saturated sodium thiosulfate solution and 20 mL of water. The organic layer is separated and the organic phase is distilled off to get the compound (V').

Yield: 0.25 g of white powder.

The equilibrium between (2S,4R)-4-(tert-butyldimethylsilyloxy)-6-oxo-tetrahydro-2H-pyran-2-carbaldehyde (IV') and its hydrate (V') as studied by NMR spectroscopy proves that in chlorinated hydrocarbons: chloroform, dichloromethane; hydrocarbons: pentane, hexane, heptane, methylcyclohexane and cyclohexane and particularly in aromatic hydrocarbons: toluene (or its chlorinated analogues) the equilibrium is shifted completely towards aldehyde. Use of toluene as the solvent for the Wittig reaction significantly increases the yield compared to the commonly used THF because in THF aldehyde and hydrate are present in approximately equal amounts while aromatic hydrocarbons favour the aldehyde.

The isolated hydrate form of aldehyde has the following NMR spectra:

$^1$H-NMR (300 MHz, THF-d$_8$) δ: 5.27 (d, J=6 Hz, 1H, OH), 5.19 (d, J=6 Hz, 1H, OH), 4.90-4.85 (m, 1H), 4.44-4.38 (m, 2H), 2.58 (dd, J=17 Hz, J=4 Hz,1H), 2.44-2.36 (m, 1H), 1.92-1.87 (m, 2H), 0.91 (s, 9H), 0.10 (s, 6H).

$^{13}$C-NMR (75 MHz, THF-d$_8$) δ: 168.7, 91.7, 79.0, 65.1, 40.3, 31.0, 26.2, 18.7, −4.8, −4.8.

The aldehyde formed in an aprotic solvent has the following NMR spectra:

$^1$H-NMR (300 MHz, CDCl$_3$) δ: 9.82 (s, 1H), 5.09 (dd, J=11 Hz, J=4 Hz,1H), 4.38 (m, 1H), 2.67 (d, J=4 Hz, 2H), 2.18-2.10 (m, 1H), 1.91-1.81 (m, 1H), 0.89 (s, 9H), 0.09 (s, 6H).

$^{13}$C-NMR (75 MHz, CDCl$_3$) δ: 199.4, 168.0, 79.2, 62.9, 39.6, 31.4, 25.6, 17.9, −4.9.

The obtained (4R,6S)-4-(tert-butyldimethylsilyloxy)-6-(dihydroxymethyl)tetrahydro-2H-pyran-2-one (V') is used in the next step without further purification by dissolution in toluene where dehydration to (2S,4R)-4-(tert-butyldimethylsilyloxy)-6-oxo-tetrahydro-2H-pyran-2-carbaldehyde (IV') occurs.

EXAMPLE 4

Example 4.1

Preparation of N-(5-((E)-2-((2S,4R)-4-(tert-butyldimethylsilyloxy)-6-oxotetrahydro-2H-pyran-2-yl)vinyl)-4-(4-fluorophenyl)-6-isopropylpyrimidin-2-yl)-N-methylmethanesulfonamide (VII')

To a stirred suspension of ((4-(4-fluorophenyl)-6-isopropyl-2-(N-methylmethyl-sulfonamido)pyrimidin-5-yl)methyl)tributylphosphonium 2,2,2-trifluoro-acetate (VI') (504 mg, 0.77 mmol) at room temperature in dry toluene (8 mL), sodium hexamethyldisilazane in toluene (1.3 mL of 0.6 M, 0.77 mmol) is added portionwise in 10 minutes. The reaction mixture is stirred for 60 min and treated at room temperature with a solution of (2S,4R)-4-(tert-butyldimethylsilyl oxy)-6-oxo-tetrahydro-2H-pyran-2-carbaldehyde (IV') (200 mg, 0.77 mmol) in 25 mL of dry toluene obtained by dissolution of (4R,6S)-4-(tert-butyldimethylsilyloxy)-6-(dihydroxymethyl)-tetrahydropyran-2-one (V') (214 mg, 0.77 mmol) in toluene and removal of released water. After 24 hours of stirring at room temperature the solution is treated with saturated ammonium chloride solution or water. The aqueous phase is extracted with $^t$BuMeO (2×20 mL), and the combined organic layers dried and concentrated. The residue is purified by silica gel chromatography (elution with $^t$BuMeO/hexane mixture) to give 273 mg (61%) of N-(5-((E)-2-((2S, 4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methylmethanesulfonamide as a white solid.

$^1$H-NMR (300 MHz, CDCl$_3$) δ: 7.62 (dd, J=9 Hz, J=5 Hz, 2H), 7.09 (t, J=9Hz, 2H), 6.69 (dd, J=16 Hz, J=1 Hz, 1H), 5.49 (dd, J=16 Hz, J=6 Hz, 1H), 5.22-5.16 (m, 1H), 4.29-4.27 (m, 1H), 3.56 (s, 3H), 3.50 (s, 3H), 3.32 (septet, 1H), 2.61-2.59 (m, 2H), 1.80-1.73 (m, 1H), 1.64-1.54 (m, 1H), 1.26 (d, J=7 Hz, 6H), 0.87 (s, 9H), 0.07, 0.06 (2s, 6H).

$^{13}$C-NMR (75 MHz, CDCl$_3$) δ: 174.9, 169.5, 163.5, 163.2 (d, J$_{C-F}$=250 Hz), 157.4, 134.7, 134.1, (d, J$_{C-F}$=3 Hz), 132.0 (d, J$_{C-F}$=8 Hz), 125.3, 120.5, 115.0 (d, J$_{C-F}$=22 Hz), 75.3, 63.2, 42.3, 39.2, 36.2, 33.0, 32.1, 25.5, 21.5, 17.8, −5.0, −5.0.

Example 4.2

Preparation of the Calcium Salt of (3R,5S,E)-7-(4-(4-fluorophenyl)-6-isopropyl-2-(N-methylmethylsulfonamido)pyrimidin-5-yl)-3,5-dihydroxyhept-6-enoic acid (IX)

To a stirred solution of N-(5-((E)-2-((2S,4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methylmethanesulfonamide (VII') (190 mg, 0.33 mmol) in 3 mL tetrahydrofurane, a solution of acetic acid (55 mg, 0.92 mmol) and tetra-n-butylammonium fluoride trihydrate (183 mg, 0.58 mmol) in 3 mL of tetrahydrofurane is added. The reaction mixture is stirred at 20-30° C. for 48 h, treated with 10 mL of water and extracted several times with ʹBuMeO. The combined organic layers are washed successively with the saturated NaHCO₃ solution, water and brine, dried with Na₂SO₄ and concentrated under the reduced pressure. The residue is dissolved in 3 mL of a 4:1 mixture of THF/H₂O. The clear solution is warmed to 30° C. and 8.0 M NaOH (0.044 mL, 0.35 mmol) is added portionwise. The reaction mixture is stirred at 30° C. for 2 hours giving a clear yellow solution. Then THF is removed completely under the reduced pressure (20 mbar) at 40° C. The remaining water solution is diluted with H₂O to 1.5 mL and washed with AcOEt (2×1 mL). After separation from the organic layer, the aqueous phase is distilled under the reduced pressure (20 mbar) at 40° C. to completely remove the dissolved AcOEt. The remaining clear solution of sodium rosuvastatinate (1.3 mL) is diluted with H₂O to 1.5 mL and warmed to 40° C. To a vigorously stirred solution of sodium rosuvastatinate is added dropwise Ca(OAc)₂.xH₂O (44 mg, 0.25 mmol in 0.3 mL of H₂O) over 5 minutes at 40° C. to precipitate rosuvastatin calcium (IX). After the complete addition, the suspension is stirred further for 30 minutes at 40° C. The white precipitate is filtered off. Then the wet white solid is suspended in H₂O (1 mL) and vigorously stirred for 1 hour at 20° C. The undissolved precipitate is collected by filtration, washed with H₂O (1 mL) and dried in vacuum at 40° C. to give 143 mg (87%) of rosuvastatin calcium salt (IX) as white powder.

---

The invention claimed is:

1. A process for preparing a compound of formula IV or V

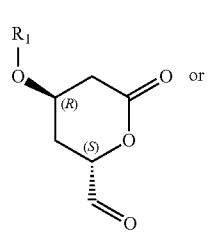

IV

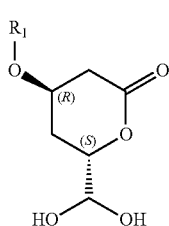

V wherein $R_1$ is a protecting group, wherein the process comprises the following steps:
a) converting a compound of formula I'

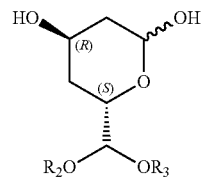

I' wherein $R_2$ and $R_3$ are independently selected from $C_1$-$C_4$-alkyl or together form a cyclic structure of formula $(CH_2)_n$ wherein n is from 2 to 6, into a compound of formula II

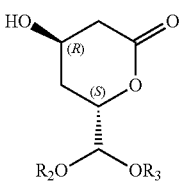

II wherein R₂ and R₃ are defined as above;
b) subsequently converting said compound obtained in step (a) into a compound of formula III $$\text{III}$$

wherein R₁ is a protecting group, R₂ and R₃ are defined as above; and
c) subsequently cleaving the acetal-compound of formula III obtained in step b).

2. The process according to claim 1, wherein R₂ and R₃ are methyl.

3. The process according to claim 1, wherein step c) is performed in an anhydrous medium to provide the compound of formula IV.

4. The process according to claim 1, wherein step c) is performed in a solvent containing water to provide the hydrate compound of formula V.

5. The process according to claim 1, wherein the compound of formula V is converted to the compound of formula IV in a solvent selected from the group consisting of aromatic hydrocarbons, aliphatic hydrocarbons, chlorinated aromatic or aliphatic hydrocarbons and aliphatic ethers.

6. The process according to claim 5, wherein the solvent is selected from the group consisting of toluene, heptane, methylcyclohexane, cyclohexane, hexane, pentane, dichloromethane, chloroform, 2-chlorotoluene, 3-chlorotoluene, 4-chlorotoluene, ᵗBuMeO, Et₂O, Me₂O and THF.

7. The process according to claim 1, further comprising the step of reacting a substrate of formula X $$\text{X}$$

wherein R₂ and R₃ are independently selected from C₁-C₄-alkyl, or together form a cyclic structure of formula (CH₂)ₙ wherein n is from 2 to 6, with acetaldehyde and an aldolase under aldol condensation conditions to form the corresponding lactol compound I'.

8. The process according to claim 7, wherein said aldolase is 2-deoxyribose-5-phosphate aldolase (DERA).

9. The process of claim 8, wherein the DERA is selected from the group of aldolases consisting of:
DERA 01 encoded by SEQ ID NO: 1 or comprising the amino acid sequence of SEQ ID NO: 2;
DERA 02 encoded by SEQ ID NO: 3 or encoded by SEQ ID NO: 4 or comprising the amino acid sequence of SEQ ID NO: 5;
DERA 03 encoded by SEQ ID NO: 6 or comprising the amino acid sequence of SEQ ID NO: 7;
DERA 04 encoded by SEQ ID NO: 8 or comprising the amino acid sequence of SEQ ID NO: 9;
DERA 05 encoded by SEQ ID NO: 10 or comprising the amino acid sequence of SEQ ID NO: 11,
DERA 06 encoded by SEQ ID NO: 12 or comprising the amino acid sequence of SEQ ID NO: 13;
DERA 07 encoded by SEQ ID NO: 14 or comprising the amino acid sequence of SEQ ID NO: 15;
DERA 08 encoded by SEQ ID NO: 16 or comprising the amino acid sequence of SEQ ID NO: 17;
DERA 09 encoded by SEQ ID NO: 18 or comprising the amino acid sequence of SEQ ID NO: 19;
DERA 10 encoded by SEQ ID NO: 20 or comprising the amino acid sequence of SEQ ID NO: 21;
DERA 11 encoded by SEQ ID NO: 22 or comprising the amino acid sequence of SEQ ID NO: 23;
DERA 12 encoded by SEQ ID NO: 24 or comprising the amino acid sequence of SEQ ID NO: 25;
DERA 13 encoded by SEQ ID NO: 26 or comprising the amino acid sequence of SEQ ID NO: 27;
DERA 14 encoded by SEQ ID NO: 28 or comprising the amino acid sequence of SEQ ID NO: 29;
DERA 15 encoded by SEQ ID NO: 30 or comprising the amino acid sequence of SEQ ID NO: 31;
DERA 16 encoded by SEQ ID NO: 32 or comprising the amino acid sequence of SEQ ID NO: 33;
DERA 17 encoded by SEQ ID NO: 34 or comprising the amino acid sequence of SEQ ID NO: 35;
DERA 18 encoded by SEQ ID NO: 36 or comprising the amino acid sequence of SEQ ID NO: 37;
DERA 19 encoded by SEQ ID NO: 38 or comprising the amino acid sequence of SEQ ID NO: 39;
DERA 20 encoded by SEQ ID NO: 40 or comprising the amino acid sequence of SEQ ID NO: 41;
DERA 21 encoded by SEQ ID NO: 42 or comprising theamino acid sequence of SEQ ID NO: 43;
DERA 22 encoded by SEQ ID NO: 44 or comprising the amino acid sequence of SEQ ID NO: 45;
DERA 23 encoded by SEQ ID NO: 46 or comprising the amino acid sequence of SEQ ID NO: 47;

and an aldolase having an amino acid sequence identity of at least about 70% of the amino acid sequence of any of SEQ ID NO: 2, SEQ ID NO: 5, SEQ ID NO: 7, SEQ ID NO: 9, SEQ ID NO: 11, SEQ ID NO: 13,SEQ ID NO: 15, SEQ ID NO: 17, SEQ ID NO: 19, SEQ ID NO: 21,SEQ ID NO: 23,SEQ ID NO: 25,SEQ ID NO: 27, SEQ ID NO: 29, SEQ ID NO: 31, SEQ ID NO: 33, SEQ ID NO: 35, SEQ ID NO: 37,SEQ ID NO: 39, SEQ ID NO: 41, SEQ ID NO: 43, SEQ ID NO: 45 or SEQ ID NO: 47.

10. The process according to claim 7, wherein said aldolase is in a living whole cell, in an inactivated whole cell, in a homogenized whole cell, in a cell free extract, is a purified enzyme, is immobilized, or is an extra-cellularly expressed protein.

11. A process for preparing an HMG COA reductase inhibitor comprising the steps of:
   a) converting a compound of formula I'

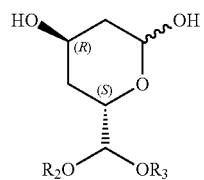

wherein $R_2$ and $R_3$ are independently selected from $C_1$-$C_4$-alkyl or together form a cyclic structure of formula $(CH_2)_n$ wherein n is from 2 to 6, into a compound of formula II

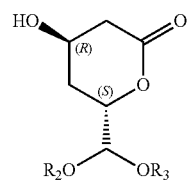

wherein $R_2$ and $R_3$ are defined as above;
   b) subsequently converting said compound obtained in step (a) into a compound of formula III

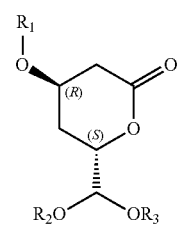

wherein $R_1$ is a protecting group, $R_2$ and $R_3$ are defined as above; and
   c) subsequently cleaving the acetal-compound of formula III obtained in step b) to obtain compound IV or V and
   d) then reacting compound IV or V in a Wittig coupling with an appropriate phosphonium salt in conditions sufficient to produce a HMG CoA reductase inhibitor or a pharmaceutically acceptable salt thereof.

12. The process according to claim 11, wherein the HMG CoA reductase inhibitor is rosuvastatin or a pharmaceutically acceptable salt thereof.

13. The process according to claim 11, wherein the step to produce a HMG CoA reductase inhibitor or a pharmaceutically acceptable salt thereof comprises the steps of:
   iia) providing a phosphonium salt having the formula VI

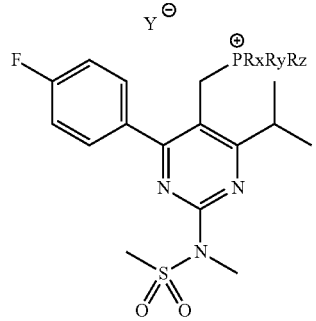

wherein Rx, Ry, and Rz, are the same or different and are selected from optionally substituted $C_1$-$C_8$-alkyl or $C_3$-$C_6$-cycloalkyl or $C_1$-$C_8$-alkenyl or $C_5$-$C_6$-cycloalkenyl or aryl,
   and Y is an anion;
   to give a compound of formula VII

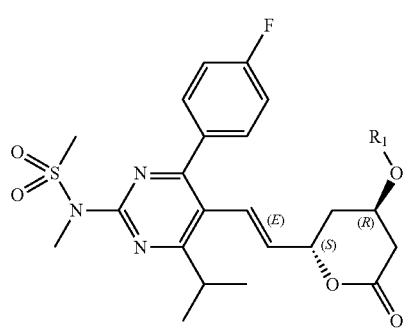

and
   iib) subsequently converting compound VII to rosuvastatin or a salt thereof.

14. The process according to claim 13, wherein Y is an anion, which is a halogen or $RCOO^-$ anion.

15. The process according to claim 14, wherein the anion is chloride, bromide or trifluoroacetate.

* * * * *

SEQUENCE LISTING

<160> NUMBER OF SEQ ID NOS: 49

<210> SEQ ID NO 1
<211> LENGTH: 780
<212> TYPE: DNA
<213> ORGANISM: Escherichia coli

<400> SEQUENCE: 1

```
atgactgatc tgaaagcaag cagcctgcgt gcactgaaat tgatggacct gaccaccctg    60
aatgacgacg acaccgacga gaaagtgatc gccctgtgtc atcaggccaa aactccggtc   120
ggcaataccg ccgctatctg tatctatcct cgctttatcc cgattgctcg caaaactctg   180
aaagagcagg gcaccccgga aatccgtatc gctacggtaa ccaacttccc acacggtaac   240
gacgacatcg acatcgcgct ggcagaaacc cgtgcggcaa tcgcctacgg tgctgatgaa   300
gttgacgttg tgttcccgta ccgcgcgctg atggcgggta acgagcaggt tggttttgac   360
ctggtgaaag cctgtaaaga ggcttgcgcg gcagcgaatg tactgctgaa agtgatcatc   420
gaaaccggcg aactgaaaga cgaagcgctg atccgtaaag cgtctgaaat ctccatcaaa   480
gcgggtgcgg acttcatcaa aacctctacc ggtaaagtgg ctgtgaacgc gacgccggaa   540
agcgcgcgca tcatgatgga agtgatccgt gatatgggcg tagaaaaaac cgttggtttc   600
aaaccggcgg gcggcgtgcg tactgcggaa gatgcgcaga aatatctcgc cattgcagat   660
gaactgttcg gtgctgactg ggcagatgcg cgtcactacc gctttggcgc ttccagcctg   720
ctggcaagcc tgctgaaagc gctgggtcac ggcgacggta agagcgccag cagctactaa   780
```

<210> SEQ ID NO 2
<211> LENGTH: 259
<212> TYPE: PRT
<213> ORGANISM: Escherichia coli

<400> SEQUENCE: 2

```
Met Thr Asp Leu Lys Ala Ser Ser Leu Arg Ala Leu Lys Leu Met Asp
1               5                   10                  15

Leu Thr Thr Leu Asn Asp Asp Asp Thr Asp Glu Lys Val Ile Ala Leu
            20                  25                  30

Cys His Gln Ala Lys Thr Pro Val Gly Asn Thr Ala Ala Ile Cys Ile
```

```
                35                  40                  45
Tyr Pro Arg Phe Ile Pro Ile Ala Arg Lys Thr Leu Lys Glu Gln Gly
    50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
            100                 105                 110

Gly Asn Glu Gln Val Gly Phe Asp Leu Val Lys Ala Cys Lys Glu Ala
        115                 120                 125

Cys Ala Ala Ala Asn Val Leu Leu Lys Val Ile Ile Glu Thr Gly Glu
    130                 135                 140

Leu Lys Asp Glu Ala Leu Ile Arg Lys Ala Ser Glu Ile Ser Ile Lys
145                 150                 155                 160

Ala Gly Ala Asp Phe Ile Lys Thr Ser Thr Gly Lys Val Ala Val Asn
                165                 170                 175

Ala Thr Pro Glu Ser Ala Arg Ile Met Met Glu Val Ile Arg Asp Met
            180                 185                 190

Gly Val Glu Lys Thr Val Gly Phe Lys Pro Ala Gly Gly Val Arg Thr
        195                 200                 205

Ala Glu Asp Ala Gln Lys Tyr Leu Ala Ile Ala Asp Glu Leu Phe Gly
    210                 215                 220

Ala Asp Trp Ala Asp Ala Arg His Tyr Arg Phe Gly Ala Ser Ser Leu
225                 230                 235                 240

Leu Ala Ser Leu Leu Lys Ala Leu Gly His Gly Asp Gly Lys Ser Ala
                245                 250                 255

Ser Ser Tyr

<210> SEQ ID NO 3
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgaatatcg cgaaaatgat cgatcatacg ctgctcaaac cggaagcgac agaacaacaa      60
atcgtgcaac tgtgcacgga agcaaagcaa tacggctttg ctccgtgtg cgtcaaccca     120 acgtgggtga aaacggcggc gcgcgagctt ccggcacgg atgtccgcgt ctgcacggtc     180
atcggctttc cacttggggc aacgacgccg gaaacaaagg cgtttgaaac aacgaacgcc     240
atcgaaaacg cgctcgcga agtcgacatg gtgatcaaca tcggcgcgtt aaaaagcggg     300
caagacgagc ttgtcgagcg cgacattcgt gcggttgtcg aagcggcggc tgcagggcg     360 cttgtcaaag tgatcgttga aacggcgctt ttgaccgatg aggaaaaagt gcgcgcctgc     420
cagctcgcag tgaaagccgg cgctgattat gtgaaaacgt cgaccgggtt ttccggcgga     480
ggtgcgacgg tggaggatgt ggcgctgatg cggaaaacgg tcggcgacag agcaggcgtc     540
aaagcatcag gcggcgtccg tgactggaaa accgctgagg cgatgatcaa cgccggcgcg     600
acgcgcatcg gcacaagctc tggggtggcg atcgtcaccg cgggacggg ccgcgctgac     660 tac                                                                   663

<210> SEQ ID NO 4
```

-continued

<211> LENGTH: 663
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgaacatcg cgaaaatgat cgatcacacc ctgctgaaac cggaagcgac cgaacagcag      60
attgttcagc tgtgcaccga agcgaaacag tatggttttg cggcggtgtg tgttaatccg     120
acctgggtta aaccgcggc gcgtgaactg agcggcaccg atgttcgtgt gtgcaccgtg      180
attggttttc cgctgggtgc gaccaccccg gaaaccaaag cgtttgaaac caccaacgcg     240
attgaaaatg gtgcgcgcga agtggatatg gtgattaaca tcggcgcgct gaaaagcggt     300
caggatgaac tggttgaacg cgatattcgt gcggttgttg aagcggcggc gggtcgcgcg     360
ctggttaaag tgattgtgga aaccgcgctg ctgaccgatg aagaaaaagt gcgtgcctgt     420
cagctggcgg ttaaagcggg tgcggattac gttaaaacca gcaccggttt tagcggtggt     480
ggtgcgaccg ttgaagatgt tgcgctgatg cgtaaaaccg ttggtgatcg tgcgggtgtg     540
aaagcgagcg gtggtgttcg cgattggaaa accgcggaag cgatgattaa tgcgggcgcg     600
acccgtattg gcaccagcag cggtgttgcg attgttaccg gtggcaccgg tcgtgcggat     660
tat                                                                   663
```

<210> SEQ ID NO 5
<211> LENGTH: 221
<212> TYPE: PRT
<213> ORGANISM: Unknown
<220> FEATURE:
<223> OTHER INFORMATION: Description of Unknown: Testek peptide

<400> SEQUENCE: 5

```
Met Asn Ile Ala Lys Met Ile Asp His Thr Leu Leu Lys Pro Glu Ala
1               5                   10                  15

Thr Glu Gln Gln Ile Val Gln Leu Cys Thr Glu Ala Lys Gln Tyr Gly
                20                  25                  30

Phe Ala Ala Val Cys Val Asn Pro Thr Trp Val Lys Thr Ala Ala Arg
            35                  40                  45

Glu Leu Ser Gly Thr Asp Val Arg Val Cys Thr Val Ile Gly Phe Pro
        50                  55                  60

Leu Gly Ala Thr Thr Pro Glu Thr Lys Ala Phe Glu Thr Thr Asn Ala
65                  70                  75                  80

Ile Glu Asn Gly Ala Arg Glu Val Asp Met Val Ile Asn Ile Gly Ala
                85                  90                  95

Leu Lys Ser Gly Gln Asp Glu Leu Val Glu Arg Asp Ile Arg Ala Val
                100                 105                 110

Val Glu Ala Ala Ala Gly Arg Ala Leu Val Lys Val Ile Val Glu Thr
            115                 120                 125

Ala Leu Leu Thr Asp Glu Glu Lys Val Arg Ala Cys Gln Leu Ala Val
        130                 135                 140

Lys Ala Gly Ala Asp Tyr Val Lys Thr Ser Thr Gly Phe Ser Gly Gly
145                 150                 155                 160

Gly Ala Thr Val Glu Asp Val Ala Leu Met Arg Lys Thr Val Gly Asp
                165                 170                 175

Arg Ala Gly Val Lys Ala Ser Gly Gly Val Arg Asp Trp Lys Thr Ala
            180                 185                 190

Glu Ala Met Ile Asn Ala Gly Ala Thr Arg Ile Gly Thr Ser Ser Gly
```

```
                195                 200                 205
Val Ala Ile Val Thr Gly Gly Thr Gly Arg Ala Asp Tyr
    210                 215                 220

<210> SEQ ID NO 6
<211> LENGTH: 666
<212> TYPE: DNA
<213> ORGANISM: Oceanobacillus iheyensis

<400> SEQUENCE: 6
atggatttag ctaaatatat tgatcatact caattaaaac cagatactac aaaacaaagt      60
attgtaaaaa ttgtggaaga ggcaaaacaa catgaatttg cttcagtatg tgttaatcca     120
cactgggttt cttactgtta taatgaatta aaagatacac cagttaaagt ttgtacagta     180
attggattcc cattaggagc cacttctact gaaacgaaaa tttttgaaac caatcaggct     240
attgctgatg gtgctacaga agtagacatg gtaattaatg tcggtgaatt aaaatcgaat     300
aatgatgctt ttgttgaaaa agacatccgt gctgttgttg aagcagcaaa aggtaaagct     360
ttaacaaaag tgataattga aacaagtctt ttaacagaag atgaaaaagt acgtgcttgt     420
aaattagcaa aaaatgcaga ggctgactat gtaaaaactt ctactgggtt ctctggtggc     480
ggcgcaactg ttgaggatat tcgcttaatg cgagagacag taggacctga atgggagtg      540 aaaagcatct ggtggtgttcg tgatttagag caaacagaaa caatgattga agctggagca     600
actagaattg gagctagttc tggggtagcg attgtctcag gagaacaagg tacatcagat     660
tactaa                                                                666

<210> SEQ ID NO 7
<211> LENGTH: 221
<212> TYPE: PRT
<213> ORGANISM: Oceanobacillus iheyensis

<400> SEQUENCE: 7

Met Asp Leu Ala Lys Tyr Ile Asp His Thr Gln Leu Lys Pro Asp Thr
1               5                   10                  15

Thr Lys Gln Ser Ile Val Lys Ile Val Glu Glu Ala Lys Gln His Glu
            20                  25                  30

Phe Ala Ser Val Cys Val Asn Pro His Trp Val Ser Tyr Cys Tyr Asn
        35                  40                  45

Glu Leu Lys Asp Thr Pro Val Lys Val Cys Thr Val Ile Gly Phe Pro
    50                  55                  60

Leu Gly Ala Thr Ser Thr Glu Thr Lys Ile Phe Glu Thr Asn Gln Ala
65                  70                  75                  80

Ile Ala Asp Gly Ala Thr Glu Val Asp Met Val Ile Asn Val Gly Glu
                85                  90                  95

Leu Lys Ser Asn Asn Asp Ala Phe Val Glu Lys Asp Ile Arg Ala Val
            100                 105                 110

Val Glu Ala Ala Lys Gly Lys Ala Leu Thr Lys Val Ile Ile Glu Thr
        115                 120                 125

Ser Leu Leu Thr Glu Asp Glu Lys Val Arg Ala Cys Lys Leu Ala Lys
    130                 135                 140

Asn Ala Glu Ala Asp Tyr Val Lys Thr Ser Thr Gly Phe Ser Gly Gly
145                 150                 155                 160

Gly Ala Thr Val Glu Asp Ile Arg Leu Met Arg Glu Thr Val Gly Pro
                165                 170                 175

Glu Met Gly Val Lys Ala Ser Gly Gly Val Arg Asp Leu Glu Gln Thr
            180                 185                 190
```

Glu Ala Met Ile Glu Ala Gly Ala Thr Arg Ile Gly Ala Ser Ser Gly
            195                 200                 205

Val Ala Ile Val Ser Gly Glu Gln Gly Thr Ser Asp Tyr
        210                 215                 220

<210> SEQ ID NO 8
<211> LENGTH: 663
<212> TYPE: DNA
<213> ORGANISM: Deinococcus radiodurans

<400> SEQUENCE: 8
atgtcactcg cctcctacat cgaccacacg ctgcttaagg ccaccgccac gctcgccgac      60
atccgcacgc tgtgtgagga agcccgcgag cactcgttct acgcggtgtg catcaacccg     120
gtctttattc cccacgcccg cgcctggctc gaaggcagcg acgtgaaggt cgccaccgtc     180
tgcggctttc ccctcggcgc catcagctcc gagcagaaag ctctggaagc ccgcctgagc     240
gccgaaacgg gcgccgacga atcgatatg gtcatccaca tcggctcggc gcttgccggc     300
gactgggacg cggtggaagc cgacgtgcgg gcagtgcgcc gcgcggtgcc cgagcaggtg     360
ctcaaggtga ttatcgaaac ctgctacctg accgacgagc aaaagcgctt ggcgactgag     420
gtcgccgtac agggcggcgc cgacttcgtg aagacgagca caggcttcgg caccggcggc     480
gccaccgtgg acgacgtgcg cctgatggcg gaagtgatcg ggggccgcgc cggactcaag     540
gcggcgggcg gcgtccgcac tcctgccgac gcgcaagcca tgatcgaggc gggcgcgacc     600
cggctgggca cctcgggcgg cgtgggtctg gtgtcgggcg cgaaaacgg agccggctac     660 tga     663

<210> SEQ ID NO 9
<211> LENGTH: 220
<212> TYPE: PRT
<213> ORGANISM: Deinococcus radiodurans

<400> SEQUENCE: 9

Met Ser Leu Ala Ser Tyr Ile Asp His Thr Leu Leu Lys Ala Thr Ala
1               5                   10                  15

Thr Leu Ala Asp Ile Arg Thr Leu Cys Glu Glu Ala Arg Glu His Ser
            20                  25                  30

Phe Tyr Ala Val Cys Ile Asn Pro Val Phe Ile Pro His Ala Arg Ala
        35                  40                  45

Trp Leu Glu Gly Ser Asp Val Lys Val Ala Thr Val Cys Gly Phe Pro
    50                  55                  60

Leu Gly Ala Ile Ser Ser Glu Gln Lys Ala Leu Glu Ala Arg Leu Ser
65                  70                  75                  80

Ala Glu Thr Gly Ala Asp Glu Ile Asp Met Val Ile His Ile Gly Ser
                85                  90                  95

Ala Leu Ala Gly Asp Trp Asp Ala Val Glu Ala Asp Val Arg Ala Val
            100                 105                 110

Arg Arg Ala Val Pro Glu Gln Val Leu Lys Val Ile Glu Thr Cys
        115                 120                 125

Tyr Leu Thr Asp Glu Gln Lys Arg Leu Ala Thr Glu Val Ala Val Gln
    130                 135                 140

Gly Gly Ala Asp Phe Val Lys Thr Ser Thr Gly Phe Gly Thr Gly Gly
145                 150                 155                 160

Ala Thr Val Asp Asp Val Arg Leu Met Ala Glu Val Ile Gly Gly Arg
                165                 170                 175

```
Ala Gly Leu Lys Ala Ala Gly Gly Val Arg Thr Pro Ala Asp Ala Gln
            180                 185                 190

Ala Met Ile Glu Ala Gly Ala Thr Arg Leu Gly Thr Ser Gly Gly Val
        195                 200                 205

Gly Leu Val Ser Gly Gly Glu Asn Gly Ala Gly Tyr
    210                 215                 220

<210> SEQ ID NO 10
<211> LENGTH: 675
<212> TYPE: DNA
<213> ORGANISM: Propionibacterium acnes

<400> SEQUENCE: 10
atgtcctctg cccccactgtc tgccaccgag ttggccggca tgatcgatca caccctgctg      60
acccctgagg ccaccacaa cgacgtcgcc aagctggtcg ccgatgccaa aaatatatggg     120 acgtggtcgg tgtgcgtatc gccatcgatg ctgccgttga acctcgacat gggtgacgtg     180
catctggccg tcgtgtgcgg gtttccgtca ggcaagcaca ccagcgcagt aaaggctgct     240
gaggctcgtg aggccatcgc cgcaggggcc gaggaggtcg acatggtgat caaccttggt     300
ctggtaaagg agggacgctg ggaggacgtc accgccgata tcgctgccgt caagcaggcc     360
gtcccggatc cgaagatcct taaggtcatt atcgagtcgg cggtgctgac cgacgacgag     420
atcgtgcggg catgccaggc tgccgagaag gccggcgccg acttcgtcaa gacgtcgacg     480
ggattccacc cacgtggcgg cgcaagcgtc gaggccgtca aggtcatggc tgacactgtt     540
ggtggacgtc tgggcgtcaa gcgtccggc ggcatccgcg actaccagac ggcatgcgcg     600
atggtcgagg ccggggcgac gcgtctagga gtttcctcga ccgccaagat ccttgccgga     660
gctcccacgg agtga                                                     675

<210> SEQ ID NO 11
<211> LENGTH: 224
<212> TYPE: PRT
<213> ORGANISM: Propionibacterium acnes

<400> SEQUENCE: 11

Met Ser Ser Ala Pro Leu Ser Ala Thr Glu Leu Ala Gly Met Ile Asp
1               5                   10                  15

His Thr Leu Leu Thr Pro Glu Ala Thr His Asn Asp Val Ala Lys Leu
            20                  25                  30

Val Ala Asp Ala Lys Lys Tyr Gly Thr Trp Ser Val Cys Val Ser Pro
        35                  40                  45

Ser Met Leu Pro Leu Asn Leu Asp Met Gly Asp Val His Leu Ala Val
    50                  55                  60

Val Cys Gly Phe Pro Ser Gly Lys His Thr Ser Ala Val Lys Ala Ala
65                  70                  75                  80

Glu Ala Arg Glu Ala Ile Ala Ala Gly Ala Glu Val Asp Met Val
                85                  90                  95

Ile Asn Leu Gly Leu Val Lys Glu Gly Arg Trp Glu Asp Val Thr Ala
            100                 105                 110

Asp Ile Ala Ala Val Lys Gln Ala Val Pro Asp Pro Lys Ile Leu Lys
        115                 120                 125

Val Ile Ile Glu Ser Ala Val Leu Thr Asp Asp Glu Ile Val Arg Ala
    130                 135                 140

Cys Gln Ala Ala Glu Lys Ala Gly Ala Asp Phe Val Lys Thr Ser Thr
145                 150                 155                 160

Gly Phe His Pro Arg Gly Gly Ala Ser Val Glu Ala Val Lys Val Met
```

```
            165                 170                 175
Ala Asp Thr Val Gly Gly Arg Leu Gly Val Lys Ala Ser Gly Gly Ile
        180                 185                 190

Arg Asp Tyr Gln Thr Ala Cys Ala Met Val Glu Ala Gly Ala Thr Arg
        195                 200                 205

Leu Gly Val Ser Ser Thr Ala Lys Ile Leu Ala Gly Ala Pro Thr Glu
        210                 215                 220

<210> SEQ ID NO 12
<211> LENGTH: 768
<212> TYPE: DNA
<213> ORGANISM: Chromobacterium violaceum

<400> SEQUENCE: 12
atgtctgcac tgattgaagc cgcgcgccgc gcgctgtccc tgatggacct gaccaccctc    60
aacgacgacg ataccgacga gaaggtggcc gcgctgtgcc gcaaggccaa gagcccggac   120
ggcaccgtgg cggcggtatg cgtgtttccc cgcttcgtgc ccatcgccaa gaagacgctg   180
cgcgaagcgg gttgtccgga ggtgcaggtg gccaccgtca ccaacttccc gcacggcaat   240
gacgacgtct ccatcgcggt ggccgaaacc cgcgccgcca tcgcctacgg cgccgacgaa   300
gtggacgtgg tgttcccgta ccgcgcgctg atggccggca accgcgacat cggcttcgag   360
ctggtcaagg cctgcaagga agcctgcggc ggcaagctct tgaaagtgat catcgagagc   420
ggcgaactga aggacgcggc gctgatccgc gaagccagcg agatttccat ccgcgccggg   480
gccgacttca tcaagacttc caccggcaag gtgccggtca cgccaccctt gcccgcggcc   540
gagaccatgc tggccgtgat caaggagcag ggcggccagt gcggcttcaa ggccgccggc   600
ggcgtcaaga gcgccaccga ggcggccgaa tacctggccc tggccgcgcg cctgctgggc   660
gaagattggg tgagcgcccg ccacttccgc ttcggcgcgt ccagcctgct ggccaatctg   720
cagatcgaga tcgccggcgg cgtcgccaag ccgagcagcg gctactga                768

<210> SEQ ID NO 13
<211> LENGTH: 255
<212> TYPE: PRT
<213> ORGANISM: Chromobacterium violaceum

<400> SEQUENCE: 13

Met Ser Ala Leu Ile Glu Ala Ala Arg Arg Ala Leu Ser Leu Met Asp
1               5                   10                  15

Leu Thr Thr Leu Asn Asp Asp Thr Asp Glu Lys Val Ala Ala Leu
            20                  25                  30

Cys Arg Lys Ala Lys Ser Pro Asp Gly Thr Val Ala Ala Val Cys Val
        35                  40                  45

Phe Pro Arg Phe Val Pro Ile Ala Lys Lys Thr Leu Arg Glu Ala Gly
    50                  55                  60

Cys Pro Glu Val Gln Val Ala Thr Val Thr Asn Phe Pro His Gly Asn
65                  70                  75                  80

Asp Asp Val Ser Ile Ala Val Ala Glu Thr Arg Ala Ala Ile Ala Tyr
                85                  90                  95

Gly Ala Asp Glu Val Asp Val Val Phe Pro Tyr Arg Ala Leu Met Ala
            100                 105                 110

Gly Asn Arg Asp Ile Gly Phe Glu Leu Val Lys Ala Cys Lys Glu Ala
        115                 120                 125

Cys Gly Gly Lys Leu Leu Lys Val Ile Ile Glu Ser Gly Glu Leu Lys
    130                 135                 140
```

```
Asp Ala Ala Leu Ile Arg Glu Ala Ser Glu Ile Ser Ile Arg Ala Gly
145                 150                 155                 160

Ala Asp Phe Ile Lys Thr Ser Thr Gly Lys Val Pro Val Asn Ala Thr
            165                 170                 175

Leu Pro Ala Ala Glu Thr Met Leu Ala Val Ile Lys Glu Gln Gly Gly
        180                 185                 190

Gln Cys Gly Phe Lys Ala Ala Gly Val Lys Ser Ala Thr Glu Ala
    195                 200                 205

Ala Glu Tyr Leu Ala Leu Ala Ala Arg Leu Leu Gly Glu Asp Trp Val
210                 215                 220

Ser Ala Arg His Phe Arg Phe Gly Ala Ser Ser Leu Leu Ala Asn Leu
225                 230                 235                 240

Gln Ile Glu Ile Ala Gly Gly Val Ala Lys Pro Ser Ser Gly Tyr
            245                 250                 255
```

<210> SEQ ID NO 14
<211> LENGTH: 780
<212> TYPE: DNA
<213> ORGANISM: Agrobacterium tumefaciens

<400> SEQUENCE: 14

```
gtgaccatgg aactccagcg tccgcgcgaa gcggctgccc tcactttgtc cttgctggac     60
ctgaccaatc ttagggaaga ctgcacgccg cagcagatcg caaccctctg ccagcgggcg    120
catacggagt ttggcaacac cgctgccatt tgcatctggc cgcgtttcgt cgcgcaggcc    180
cgagcggcgt tcggaaaaga ccacacgatt cgcatcgcaa cggtcgtgaa tttcccctcc    240
ggcgatctcg atgtcgcgac cgtggttgcg gaaacggaag ctgcaatcgg cgatggcgcc    300
gacgaaatcg atctggtcat tccctatcgt aaattcatgg caggcgatga atcggcggtg    360
gccgaaatga tcgcggccgt gcgtaaggct tgcgcggcac ctgtgttgct caaggtcatt    420
cttgagaccg gtgagctgaa ggacaaggcc ctgatccgcc gtgcctcgga atcgccatt     480
gccgaagggg cggatttcat caagacctcg accggcaagg tcgccgtcaa tgccacgctg    540
gaagcggccg atatcatgct gcaggcgatc cgggacagca aaagaaggt gggcttcaag     600
ccggccggcg gcatcggcac ggtggaggac gcgacactat acctgcggct ggcggaaacc    660
atcatggcgc ccaactgggc catgccgtcg accttccgtt tcggtgcctc gggcgtcctc    720
gatgatgtgc tgaacgtgct ggccggcggc gaaccggcca aggccgccag cgggtattga    780
```

<210> SEQ ID NO 15
<211> LENGTH: 259
<212> TYPE: PRT
<213> ORGANISM: Agrobacterium tumefaciens

<400> SEQUENCE: 15

```
Met Thr Met Glu Leu Gln Arg Pro Arg Glu Ala Ala Ala Leu Thr Leu
1               5                   10                  15

Ser Leu Leu Asp Leu Thr Asn Leu Arg Glu Asp Cys Thr Pro Gln Gln
            20                  25                  30

Ile Ala Thr Leu Cys Gln Arg Ala His Thr Glu Phe Gly Asn Thr Ala
        35                  40                  45

Ala Ile Cys Ile Trp Pro Arg Phe Val Ala Gln Ala Arg Ala Ala Phe
    50                  55                  60

Gly Lys Asp His Thr Ile Arg Ile Ala Thr Val Val Asn Phe Pro Ser
65                  70                  75                  80

Gly Asp Leu Asp Val Ala Thr Val Val Ala Glu Thr Glu Ala Ala Ile
                85                  90                  95
```

Gly Asp Gly Ala Asp Glu Ile Asp Leu Val Ile Pro Tyr Arg Lys Phe
            100                 105                 110

Met Ala Gly Asp Glu Ser Ala Val Ala Glu Met Ile Ala Ala Val Arg
            115                 120                 125

Lys Ala Cys Ala Ala Pro Val Leu Leu Lys Val Ile Leu Glu Thr Gly
            130                 135                 140

Glu Leu Lys Asp Lys Ala Leu Ile Arg Arg Ala Ser Glu Ile Ala Ile
145                 150                 155                 160

Ala Glu Gly Ala Asp Phe Ile Lys Thr Ser Thr Gly Lys Val Ala Val
                165                 170                 175

Asn Ala Thr Leu Glu Ala Ala Asp Ile Met Leu Gln Ala Ile Arg Asp
            180                 185                 190

Ser Lys Lys Lys Val Gly Phe Lys Pro Ala Gly Gly Ile Gly Thr Val
            195                 200                 205

Glu Asp Ala Thr Leu Tyr Leu Arg Leu Ala Glu Thr Ile Met Ala Pro
    210                 215                 220

Asn Trp Ala Met Pro Ser Thr Phe Arg Phe Gly Ala Ser Gly Val Leu
225                 230                 235                 240

Asp Asp Val Leu Asn Val Leu Ala Gly Gly Glu Pro Ala Lys Ala Ala
                245                 250                 255

Ser Gly Tyr

<210> SEQ ID NO 16
<211> LENGTH: 681
<212> TYPE: DNA
<213> ORGANISM: Anabaena variabilis

<400> SEQUENCE: 16
atggcagcag actatccgaa cattgatatt gcgccattta tcgatcacgc cctgttaacg        60
ccaacggcta ctccagagca ggttgaccaa tggtgtgaac aagcagacag atataatttt       120
gcgtcggttt gtttgtatcc tacttatgta aaacaagcag cagaatttct ccacggcaag       180
aaacctaagg tttgtacggt aattggtttt cctactgggg ctacgactcg ctcagtcaag       240
ttgtatgagg cactggaagc ggtggagaat ggagccacag agctagatgt agtcatcaat       300
ttgggctgct tgaaatctgg taatacggaa gcagtacacc gggaaattgc cgaaatttgc       360
gaagagactg acaagtagt taaagtaatt ttggaaacaa acttactgac ggatgcagaa       420
aaaaaaatcg cggccgatat agcaatggat gcaggagcca cattcttaaa aaccaataca       480
ggttggaatg gcggtgctac agtggcagat gtgcggcttt taaagaaat cacacgggaa       540 agggtgggta taaaggcatc tggtgggatt cgcaccctca atcaagcctt agacttaata       600
ttagcgggtg cgactagatt aggtacgtct cgtggtatcg atttaatcca ccagcgagat       660
aacccggaaa aagttgaata g                                                 681

<210> SEQ ID NO 17
<211> LENGTH: 226
<212> TYPE: PRT
<213> ORGANISM: Anabaena variabilis

<400> SEQUENCE: 17

Met Ala Ala Asp Tyr Pro Asn Ile Asp Ile Ala Pro Phe Ile Asp His
1               5                   10                  15

Ala Leu Leu Thr Pro Thr Ala Thr Pro Glu Gln Val Asp Gln Trp Cys
            20                  25                  30

Glu Gln Ala Asp Arg Tyr Asn Phe Ala Ser Val Cys Leu Tyr Pro Thr

```
                35                  40                  45
Tyr Val Lys Gln Ala Ala Glu Phe Leu His Gly Lys Lys Pro Lys Val
 50                  55                  60

Cys Thr Val Ile Gly Phe Pro Thr Gly Ala Thr Arg Ser Val Lys
 65                  70                  75                  80

Leu Tyr Glu Ala Leu Glu Ala Val Glu Asn Gly Ala Thr Glu Leu Asp
                 85                  90                  95

Val Val Ile Asn Leu Gly Cys Leu Lys Ser Gly Asn Thr Glu Ala Val
            100                 105                 110

His Arg Glu Ile Ala Glu Ile Cys Glu Glu Thr Gly Gln Val Val Lys
        115                 120                 125

Val Ile Leu Glu Thr Asn Leu Leu Thr Asp Ala Glu Lys Lys Ile Ala
    130                 135                 140

Ala Asp Ile Ala Met Asp Ala Gly Ala Thr Phe Leu Lys Thr Asn Thr
145                 150                 155                 160

Gly Trp Asn Gly Gly Ala Thr Val Ala Asp Val Arg Leu Leu Lys Glu
                165                 170                 175

Ile Thr Arg Glu Arg Val Gly Ile Lys Ala Ser Gly Gly Ile Arg Thr
            180                 185                 190

Leu Asn Gln Ala Leu Asp Leu Ile Leu Ala Gly Ala Thr Arg Leu Gly
        195                 200                 205

Thr Ser Arg Gly Ile Asp Leu Ile His Gln Arg Asp Asn Pro Glu Lys
    210                 215                 220

Val Glu
225

<210> SEQ ID NO 18
<211> LENGTH: 681
<212> TYPE: DNA
<213> ORGANISM: Pseudomonas syringae

<400> SEQUENCE: 18
atgaattcgc tcgaacccgc tgcactggcc caggccatcg atcacacctt gttggcggcg      60
gatgccagcc gagagcagat tgccacgctt tgcgcagaag cccgggaaca cggcttctac     120
tcggtgtgcg tgaactccag ccaggtgcct tttgccgccc gacaactggc cgggtctgcc     180
gtgaaggtct gtgcggtggt gggctttccg ctgggcgccg gctgagtgc agcaaggcg      240 tcggaagcag ccctgacgat cgccgccggg gctcaggaaa tcgacatggt gctgaacatc     300
ggctggctca aggacggtct gttcgatgag gtccgcgacg atatcgccgc ggtgctgcaa     360
gcctgtggca aggtgccgct caaggtgatc ctggaaacct gcctgctcga tgaggcgcag     420
aaggtgcgcg cctgcgagat ctgccgcgag ctgggcgtgg cattcgtcaa gacctccact     480
ggcttcagcc gcagcggcgc gacgctcgag gatgtggcgc tgatgcgccg tgtggtaggc     540
cctgacatcg gcgtcaaggc gtctggcggg gtgcgtgacg tggccacggc cagagcgatg     600
atcgaagctg gcgcaacgcg cctgggcacc agttccggga ttgcgatcgt gaccggcgca     660
ggtacggggg cgggttattg a                                                681

<210> SEQ ID NO 19
<211> LENGTH: 226
<212> TYPE: PRT
<213> ORGANISM: Pseudomonas syringae

<400> SEQUENCE: 19

Met Asn Ser Leu Glu Pro Ala Ala Leu Ala Gln Ala Ile Asp His Thr
 1               5                  10                  15
```

-continued

```
Leu Leu Ala Ala Asp Ala Ser Arg Glu Gln Ile Ala Thr Leu Cys Ala
            20                  25                  30

Glu Ala Arg Glu His Gly Phe Tyr Ser Val Cys Val Asn Ser Ser Gln
        35                  40                  45

Val Pro Phe Ala Ala Arg Gln Leu Ala Gly Ser Ala Val Lys Val Cys
    50                  55                  60

Ala Val Val Gly Phe Pro Leu Gly Ala Gly Leu Ser Ala Ser Lys Ala
65                  70                  75                  80

Ser Glu Ala Ala Leu Thr Ile Ala Ala Gly Ala Gln Glu Ile Asp Met
                85                  90                  95

Val Leu Asn Ile Gly Trp Leu Lys Asp Gly Leu Phe Asp Glu Val Arg
            100                 105                 110

Asp Asp Ile Ala Ala Val Leu Gln Ala Cys Gly Lys Val Pro Leu Lys
        115                 120                 125

Val Ile Leu Glu Thr Cys Leu Leu Asp Glu Ala Gln Lys Val Arg Ala
    130                 135                 140

Cys Glu Ile Cys Arg Glu Leu Gly Val Ala Phe Val Lys Thr Ser Thr
145                 150                 155                 160

Gly Phe Ser Arg Ser Gly Ala Thr Leu Glu Asp Val Ala Leu Met Arg
                165                 170                 175

Arg Val Val Gly Pro Asp Ile Gly Val Lys Ala Ser Gly Gly Val Arg
            180                 185                 190

Asp Val Ala Thr Ala Arg Ala Met Ile Glu Ala Gly Ala Thr Arg Leu
        195                 200                 205

Gly Thr Ser Ser Gly Ile Ala Ile Val Thr Gly Ala Gly Thr Gly Ala
    210                 215                 220

Gly Tyr
225

<210> SEQ ID NO 20
<211> LENGTH: 669
<212> TYPE: DNA
<213> ORGANISM: Erwinia carotovora

<400> SEQUENCE: 20
atgactgact acgcacgcta tatcgaccac accctgctgg cagcaaatgc caccgaacag      60
caaatcgtca cgctgtgcga tgaagcgata gcgcaccatt tttatgccgt ctgtgttaat     120
tccggctacg ttcccttagt agctgaaaaa ttgaaaggtt cagcggtaca ggtgtgctcg     180
gttattggat ttcctctcgg tgcaggcctg acttccagca aagcatttga agcgaaagcc     240
gcgattgatg ccggtgcaca ggaaatcgac atggtgatta acgtcggctg gctgaaaagc     300
gggaagattg atgccgtcaa agcggatatt caggccgtgc gtggggtttg cgccgctata     360
ccgttgaagg taatattgga aacctgtctg cttgatgacg aacagattgt gctggtgtgt     420
gaaatgtgtc gtcagttgga tgtcgcgttc gtcaaaacgt ctaccggttt cagcaccgac     480
ggcgcacgcg aagaacacgt tcgactgatg cgtagcactg tcggcagcga gatgggtgta     540
aaagcctccg gcgcggttcg cgatcgcgaa acggcacaac gaatgattga agcaggcgcc     600
acgcgtattg gcaccagttc aggcgttgct atcgtttctg atgacgctgc cgcagcaggg     660
aactactaa                                                             669

<210> SEQ ID NO 21
<211> LENGTH: 222
<212> TYPE: PRT
<213> ORGANISM: Erwinia carotovora
```

<400> SEQUENCE: 21

Met Thr Asp Tyr Ala Arg Tyr Ile Asp His Thr Leu Leu Ala Ala Asn
1               5                   10                  15

Ala Thr Glu Gln Gln Ile Val Thr Leu Cys Asp Glu Ala Ile Ala His
            20                  25                  30

His Phe Tyr Ala Val Cys Val Asn Ser Gly Tyr Val Pro Leu Val Ala
        35                  40                  45

Glu Lys Leu Lys Gly Ser Ala Val Gln Val Cys Ser Val Ile Gly Phe
    50                  55                  60

Pro Leu Gly Ala Gly Leu Thr Ser Ser Lys Ala Phe Glu Ala Lys Ala
65                  70                  75                  80

Ala Ile Asp Ala Gly Ala Gln Glu Ile Asp Met Val Ile Asn Val Gly
            85                  90                  95

Trp Leu Lys Ser Gly Lys Ile Asp Ala Val Lys Ala Asp Ile Gln Ala
            100                 105                 110

Val Arg Gly Val Cys Ala Ala Ile Pro Leu Lys Val Ile Leu Glu Thr
        115                 120                 125

Cys Leu Leu Asp Asp Glu Gln Ile Val Leu Val Cys Glu Met Cys Arg
130                 135                 140

Gln Leu Asp Val Ala Phe Val Lys Thr Ser Thr Gly Phe Ser Thr Asp
145                 150                 155                 160

Gly Ala Arg Glu Glu His Val Arg Leu Met Arg Ser Thr Val Gly Ser
                165                 170                 175

Glu Met Gly Val Lys Ala Ser Gly Ala Val Arg Asp Arg Glu Thr Ala
            180                 185                 190

Gln Arg Met Ile Glu Ala Gly Ala Thr Arg Ile Gly Thr Ser Ser Gly
        195                 200                 205

Val Ala Ile Val Ser Asp Asp Ala Ala Ala Gly Asn Tyr
    210                 215                 220

<210> SEQ ID NO 22
<211> LENGTH: 684
<212> TYPE: DNA
<213> ORGANISM: Desulfotalea psychrophila

<400> SEQUENCE: 22
atgaatacaa tcattagccc gaaagaaatt gccttgtata ttgatcacac tctcctcaaa      60
cctgaggcaa gccctgcagc tattcgtacc ctatgcgcag aagctcgtga gtactctttc    120
aagactgtat gcgtcaactc ttgctatgtc cctctctgtg tggaagaact tcaagcttgc    180
cccgttgatg tttgctcggt ggtgggttc ccacttgggg ctatgctgag ttcggcaaag    240
gcctacgagg caaaacttgc agtggcagcc ggggccgacg aaattgatat ggttatcaat    300
attggtctct tgaaggcagg agaacttgaa gctgttcggg cagatattga aacagttttt    360
gccgcctgtg gagaggcaga ccttaaggtg atcattgaga caggcctgct cagcgatgcg    420
gagaaaaaaa gcgtctgtca gatatgcaag gaagttggtg tcgcctttgt taagacctcc    480
acgggttttg gtcatggtgg cgcaaccgtt gccgatgtag aacttatgcg tgctgttgtt    540
ggtgagagat gtaaggttaa ggcctctggc ggggtacgca accttgccga tgcccgcgcc    600
ctgatagcgg caggagccaa tagaattggg gcaagtgccg gtatcgcaat tgtcaatgga    660
gaagaggtcc cccttctcg ttaa                                             684

<210> SEQ ID NO 23
<211> LENGTH: 227

```
<212> TYPE: PRT
<213> ORGANISM: Desulfotalea psychrophila

<400> SEQUENCE: 23

Met Asn Thr Ile Ile Ser Pro Lys Glu Ile Ala Leu Tyr Ile Asp His
1               5                   10                  15

Thr Leu Leu Lys Pro Glu Ala Ser Pro Ala Ala Ile Arg Thr Leu Cys
            20                  25                  30

Ala Glu Ala Arg Glu Tyr Ser Phe Lys Thr Val Cys Val Asn Ser Cys
        35                  40                  45

Tyr Val Pro Leu Cys Val Glu Glu Leu Gln Ala Cys Pro Val Asp Val
    50                  55                  60

Cys Ser Val Val Gly Phe Pro Leu Gly Ala Met Leu Ser Ser Ala Lys
65                  70                  75                  80

Ala Tyr Glu Ala Lys Leu Ala Val Ala Ala Gly Ala Asp Glu Ile Asp
                85                  90                  95

Met Val Ile Asn Ile Gly Leu Leu Lys Ala Gly Glu Leu Glu Ala Val
            100                 105                 110

Arg Ala Asp Ile Glu Thr Val Phe Ala Ala Cys Gly Glu Ala Asp Leu
        115                 120                 125

Lys Val Ile Ile Glu Thr Gly Leu Leu Ser Asp Ala Glu Lys Lys Ser
    130                 135                 140

Val Cys Gln Ile Cys Lys Glu Val Gly Val Ala Phe Val Lys Thr Ser
145                 150                 155                 160

Thr Gly Phe Gly His Gly Gly Ala Thr Val Ala Asp Val Glu Leu Met
                165                 170                 175

Arg Ala Val Val Gly Glu Arg Cys Lys Val Lys Ala Ser Gly Gly Val
            180                 185                 190

Arg Asn Leu Ala Asp Ala Arg Ala Leu Ile Ala Ala Gly Ala Asn Arg
        195                 200                 205

Ile Gly Ala Ser Ala Gly Ile Ala Ile Val Asn Gly Glu Glu Val Pro
    210                 215                 220

Pro Ser Arg
225

<210> SEQ ID NO 24
<211> LENGTH: 636
<212> TYPE: DNA
<213> ORGANISM: Bacillus subtilis

<400> SEQUENCE: 24
atgtcattag ccaacataat tgatcataca gctttgaaac cgcatacaca aaaagcggac        60
attctaaaac taattgaaga agcgaaaaca tacaaatttg cttcagtatg tgtcaatccg       120
acatgggtgg agcttgctgc aaaagagctt aagggaactg gagtcgacgt tgtacggtc        180 atcggcttcc cgctcggtgc caatacaact gaaacaaaag cgttcgaaac aaaagacgcc       240
atttcaaaag gcgccactga agtggatatg gtcattaata ttgccgcttt aaaagacaag       300
gaagacgatg tggtggaagc tgatatccgc ggtgtagtgg aagctgtagc cggaaaagcg       360
cttgtcaaag tcattatcga aacgtgcctt ctgactgatg aagaaaaaga acgtgcatgc       420
cgtttagcgg tgtctgcggg agcggatttc gtaaaaacat caacaggctt ttctacaggc       480
ggcgcaacga aggaagatat cgccttaatg cgcaaaacag tagggcctga tatcggcgtg       540
aaagcatctg gcggcgtcag aacgaaagaa gatgtagaca caatggtaga ggccggagca       600
agccgaattg cgccagcgca ggcgtttcta tcgtaa                                  636
```

<210> SEQ ID NO 25
<211> LENGTH: 211
<212> TYPE: PRT
<213> ORGANISM: Bacillus subtilis

<400> SEQUENCE: 25

```
Met Ser Leu Ala Asn Ile Ile Asp His Thr Ala Leu Lys Pro His Thr
1               5                   10                  15

Gln Lys Ala Asp Ile Leu Lys Leu Ile Glu Glu Ala Lys Thr Tyr Lys
            20                  25                  30

Phe Ala Ser Val Cys Val Asn Pro Thr Trp Val Glu Leu Ala Ala Lys
        35                  40                  45

Glu Leu Lys Gly Thr Gly Val Asp Val Cys Thr Val Ile Gly Phe Pro
    50                  55                  60

Leu Gly Ala Asn Thr Thr Glu Thr Lys Ala Phe Glu Thr Lys Asp Ala
65                  70                  75                  80

Ile Ser Lys Gly Ala Thr Glu Val Asp Met Val Ile Asn Ile Ala Ala
                85                  90                  95

Leu Lys Asp Lys Glu Asp Val Val Glu Ala Asp Ile Arg Gly Val
            100                 105                 110

Val Glu Ala Val Ala Gly Lys Ala Leu Val Lys Val Ile Glu Thr
        115                 120                 125

Cys Leu Leu Thr Asp Glu Glu Lys Glu Arg Ala Cys Arg Leu Ala Val
130                 135                 140

Ser Ala Gly Ala Asp Phe Val Lys Thr Ser Thr Gly Phe Ser Thr Gly
145                 150                 155                 160

Gly Ala Thr Lys Glu Asp Ile Ala Leu Met Arg Lys Thr Val Gly Pro
                165                 170                 175

Asp Ile Gly Val Lys Ala Ser Gly Gly Val Arg Thr Lys Glu Asp Val
            180                 185                 190

Asp Thr Met Val Glu Ala Gly Ala Ser Arg Ile Ala Pro Ala Gln Ala
        195                 200                 205

Phe Leu Ser
    210
```

<210> SEQ ID NO 26
<211> LENGTH: 672
<212> TYPE: DNA
<213> ORGANISM: Listeria innocua

<400> SEQUENCE: 26

```
atgacaattg ccaaaatgat cgaccacact gctttaaaac agacacaac  gaaagaacaa    60
attttaacat taacaaaaga agcaagagaa tatggttttg cttccgtatg cgtgaatcca   120
acttgggtga aattatccgc tgaacagctt tcaggagcag aatccgttgt atgtacagtt   180
atcggtttcc cacttggagc aaatacacca gaagtaaaag cttttgaagt gaaaaatgcc   240
atcgaaaacg gcgctaaaga agtggatatg gttattaata tcggcgcatt aaaagacaaa   300
gacgatgaat tagtagaacg tgatattcgt gctgtagttg atgctgccaa agggaaagca   360
ttagtaaaag taattattga aacttgccta ttaacagacg aagaaaaagt tcgcgcatgt   420
gaaatcgctg taaaagcagg aacagacttc gttaaaacat ccactggatt ctccacaggt   480
ggcgcaactg ccgaagatat tgctttaatg cgtaaaactg taggaccaaa catcggcgta   540
aaagcatctg gcggagttcg tacaaaagaa gacgtagaaa aaatgattga agcaggtgca   600
actcgtatcg gcgcaagtgc aggtgtcgca attgtttccg gcgaaaaacc agctaaacca   660
```
gataattact aa                                                          672

<210> SEQ ID NO 27
<211> LENGTH: 223
<212> TYPE: PRT
<213> ORGANISM: Listeria innocua

<400> SEQUENCE: 27

Met Thr Ile Ala Lys Met Ile Asp His Thr Ala Leu Lys Pro Asp Thr
1               5                   10                  15

Thr Lys Glu Gln Ile Leu Thr Leu Thr Lys Glu Ala Arg Glu Tyr Gly
            20                  25                  30

Phe Ala Ser Val Cys Val Asn Pro Thr Trp Val Lys Leu Ser Ala Glu
        35                  40                  45

Gln Leu Ser Gly Ala Glu Ser Val Val Cys Thr Val Ile Gly Phe Pro
    50                  55                  60

Leu Gly Ala Asn Thr Pro Glu Val Lys Ala Phe Glu Val Lys Asn Ala
65                  70                  75                  80

Ile Glu Asn Gly Ala Lys Glu Val Asp Met Val Ile Asn Ile Gly Ala
                85                  90                  95

Leu Lys Asp Lys Asp Asp Glu Leu Val Glu Arg Asp Ile Arg Ala Val
            100                 105                 110

Val Asp Ala Ala Lys Gly Lys Ala Leu Val Lys Val Ile Ile Glu Thr
        115                 120                 125

Cys Leu Leu Thr Asp Glu Glu Lys Val Arg Ala Cys Glu Ile Ala Val
    130                 135                 140

Lys Ala Gly Thr Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                165                 170                 175

Asn Ile Gly Val Lys Ala Ser Gly Gly Val Arg Thr Lys Glu Asp Val
            180                 185                 190

Glu Lys Met Ile Glu Ala Gly Ala Thr Arg Ile Gly Ala Ser Ala Gly
        195                 200                 205

Val Ala Ile Val Ser Gly Glu Lys Pro Ala Lys Pro Asp Asn Tyr
    210                 215                 220

<210> SEQ ID NO 28
<211> LENGTH: 648
<212> TYPE: DNA
<213> ORGANISM: Clostridium acetobutylicum

<400> SEQUENCE: 28
atgaatattg ctaaaattat agatcataca gcattaaagc cagatacaac aaaggagcag      60
atactaaaac taatagaaga agctaaacaa ataactttg catcagtttg tgtaaatcca     120
aagtgggtta agaggcaag ctgtgcatta aggacagca gtgttaaagt gtgtactgta      180
ataggggttc ctcttggagc taatacaact gctacaaaag tatttgaaac acaagatgct     240
attaaaaatg gtgcagaaga agtagatatg gttgtttcta taggaattt aaaagataaa     300 aatgatgatt atgtagaaaa agatatagaa gaagttgtta aggcagctag tggaaaggcc     360
ttagttaaag taattattga aacttgtctt cttaccgaag aagagaagat aagagcgtgt     420
aaactagcta aaaaagcagg tgcagatttt gttaaaacat caacagggtt ttcaacagga     480
ggggctaagg cagaagatat taaattaatg agaaaaacag ttggagctgg tatgggagtt     540
aaggcctcag gtggtattca tacaagagaa gaagcaatta aacttataga agctggagct     600
acacgtattg gagctagtgc aagtatagat ataatttcag aaaattaa 648

<210> SEQ ID NO 29
<211> LENGTH: 215
<212> TYPE: PRT
<213> ORGANISM: Clostridium acetobutylicum

<400> SEQUENCE: 29

```
Met Asn Ile Ala Lys Ile Ile Asp His Thr Ala Leu Lys Pro Asp Thr
1               5                   10                  15

Thr Lys Glu Gln Ile Leu Lys Leu Ile Glu Glu Ala Lys Gln Asn Asn
            20                  25                  30

Phe Ala Ser Val Cys Val Asn Pro Lys Trp Val Lys Glu Ala Ser Cys
        35                  40                  45

Ala Leu Lys Asp Ser Ser Val Lys Val Cys Thr Val Ile Gly Phe Pro
    50                  55                  60

Leu Gly Ala Asn Thr Thr Ala Thr Lys Val Phe Glu Thr Gln Asp Ala
65                  70                  75                  80

Ile Lys Asn Gly Ala Glu Val Asp Met Val Val Ser Ile Gly Glu
                85                  90                  95

Leu Lys Asp Lys Asn Asp Asp Tyr Val Glu Lys Asp Ile Glu Val
                100                 105                 110

Val Lys Ala Ala Ser Gly Lys Ala Leu Val Lys Val Ile Ile Glu Thr
            115                 120                 125

Cys Leu Leu Thr Glu Glu Lys Ile Arg Ala Cys Lys Leu Ala Lys
    130                 135                 140

Lys Ala Gly Ala Asp Phe Val Lys Thr Ser Thr Gly Phe Ser Thr Gly
145                 150                 155                 160

Gly Ala Lys Ala Glu Asp Ile Lys Leu Met Arg Lys Thr Val Gly Ala
                165                 170                 175

Gly Met Gly Val Lys Ala Ser Gly Gly Ile His Thr Arg Glu Glu Ala
                180                 185                 190

Ile Lys Leu Ile Glu Ala Gly Ala Thr Arg Ile Gly Ala Ser Ala Ser
            195                 200                 205

Ile Asp Ile Ile Ser Glu Asn
        210                 215
```

<210> SEQ ID NO 30
<211> LENGTH: 822
<212> TYPE: DNA
<213> ORGANISM: Geobacillus kaustophilus

<400> SEQUENCE: 30
atggagctca taacccagcc tagttgctgg gttttttctg tcttttttccg gagacaatac    60 ggatggctag ttttttgtcga gggagcatgg tatgatggta gacgtcagac tttccatctt    120
gacggaaatg gcagaaaggg gtttctccga atgacgatga atatcgcgaa aatgatcgat    180
catacgctgc tcaaaccgga agcgacagaa caacaaatcg tgcaactgtg cacggaagca    240
aagcaatacg gctttgcttc cgtgtgcgtc aacccaacgt gggtgaaaac ggcggcgcgc    300
gagctttccg gcacggatgt ccgcgtctgc acggtcatcg gctttccact tggggcaacg    360
acgccggaaa caaggcgtt tgaaacaacg aacgccatcg aaaacggcgc tcgcgaagtc    420
gacatggtga tcaacatcgg cgcgttaaaa agcgggcaag acgagcttgt cgagcgcgac    480
attcgtgcgg ttgtcgaagc ggcggctggc agggcgcttg tcaaagtgat cgttgaaacg    540
gcgcttttga ccgatgagga aaaagtgcgc gcctgccagc tcgcagtgaa agccggcgct    600

```
gattatgtga aaacgtcgac cgggttttcc ggcggaggtg cgacggtgga ggatgtggcg    660
ttgatgcgga aaacggtcgg cgacagagca ggcgtcaaag catcaggcgg cgtccgtgac    720
tggaaaaccg ctgaggcgat gatcaacgcc ggcgcgacgc gcatcggcac aagctctggg    780
gtggcgatcg tcaccggcgg gacgggccgc gctgactact aa                       822
```

<210> SEQ ID NO 31
<211> LENGTH: 273
<212> TYPE: PRT
<213> ORGANISM: Geobacillus kaustophilus

<400> SEQUENCE: 31

```
Met Glu Leu Ile Thr Gln Pro Ser Cys Trp Val Phe Ser Val Phe Phe
1               5                   10                  15

Arg Arg Gln Tyr Gly Trp Leu Val Phe Val Glu Gly Ala Trp Tyr Asp
            20                  25                  30

Gly Arg Arg Gln Thr Phe His Leu Asp Gly Asn Gly Arg Lys Gly Phe
        35                  40                  45

Leu Arg Met Thr Met Asn Ile Ala Lys Met Ile Asp His Thr Leu Leu
    50                  55                  60

Lys Pro Glu Ala Thr Glu Gln Gln Ile Val Gln Leu Cys Thr Glu Ala
65                  70                  75                  80

Lys Gln Tyr Gly Phe Ala Ser Val Cys Val Asn Pro Thr Trp Val Lys
                85                  90                  95

Thr Ala Ala Arg Glu Leu Ser Gly Thr Asp Val Arg Val Cys Thr Val
            100                 105                 110

Ile Gly Phe Pro Leu Gly Ala Thr Thr Pro Glu Thr Lys Ala Phe Glu
        115                 120                 125

Thr Thr Asn Ala Ile Glu Asn Gly Ala Arg Glu Val Asp Met Val Ile
    130                 135                 140

Asn Ile Gly Ala Leu Lys Ser Gly Gln Asp Glu Leu Val Glu Arg Asp
145                 150                 155                 160

Ile Arg Ala Val Val Glu Ala Ala Ala Gly Arg Ala Leu Val Lys Val
                165                 170                 175

Ile Val Glu Thr Ala Leu Leu Thr Asp Glu Glu Lys Val Arg Ala Cys
            180                 185                 190

Gln Leu Ala Val Lys Ala Gly Ala Asp Tyr Val Lys Thr Ser Thr Gly
        195                 200                 205

Phe Ser Gly Gly Gly Ala Thr Val Glu Asp Val Ala Leu Met Arg Lys
    210                 215                 220

Thr Val Gly Asp Arg Ala Gly Val Lys Ala Ser Gly Gly Val Arg Asp
225                 230                 235                 240

Trp Lys Thr Ala Glu Ala Met Ile Asn Ala Gly Ala Thr Arg Ile Gly
                245                 250                 255

Thr Ser Ser Gly Val Ala Ile Val Thr Gly Gly Thr Gly Arg Ala Asp
            260                 265                 270

Tyr
```

<210> SEQ ID NO 32
<211> LENGTH: 675
<212> TYPE: DNA
<213> ORGANISM: Bacillus halodurans

<400> SEQUENCE: 32

```
atgtcacgtt cgattgcaca atgattgat catacgctac ttaaaccaaa tacaacagaa     60
gaccaaattg taaagctctg tgaggaagca aaggaatatt catttgcatc tgtttgtgtg    120
```

-continued

```
aatcctactt gggtcgctct tgctgcgcag ttgctaaaag atgcacctga tgtgaaagta      180
tgtacagtta tcggctttcc gttaggggca acgactccgg aagtgaaagc gtttgaaacg      240
actaatgcca ttgaaaatgg agcgacagaa gtggacatgg tcattaacat tggagcgtta      300
aaagataaac aatacgagct tgttggacgc gacattcaag cggttgttaa agcagcagaa      360
gggaaagcat taacgaaagt aatcattgaa acatcgttat aacggagga agagaagaag      420 gctgcgtgtg agcttgccgt aaaagcagga gccgactttg tcaaaacgtc gactggattc      480
tctggcggag gtgctacggc tgaggatatc gcgctcatgc gaaaagtggt cggaccaaat      540
ttaggagtca aagcttctgg aggtgttaga gatctgtccg acgcgaaagc gatgattgat      600
gctggtgcta ctcggattgg tgcgagtgct ggggtggcga ttgttaacgg ggagcgtagc      660
gaagggagtt attaa                                                       675
```

<210> SEQ ID NO 33
<211> LENGTH: 224
<212> TYPE: PRT
<213> ORGANISM: Bacillus halodurans

<400> SEQUENCE: 33

```
Met Ser Arg Ser Ile Ala Gln Met Ile Asp His Thr Leu Leu Lys Pro
1               5                   10                  15

Asn Thr Thr Glu Asp Gln Ile Val Lys Leu Cys Glu Glu Ala Lys Glu
            20                  25                  30

Tyr Ser Phe Ala Ser Val Cys Val Asn Pro Thr Trp Val Ala Leu Ala
        35                  40                  45

Ala Gln Leu Leu Lys Asp Ala Pro Asp Val Lys Val Cys Thr Val Ile
    50                  55                  60

Gly Phe Pro Leu Gly Ala Thr Thr Pro Glu Val Lys Ala Phe Glu Thr
65                  70                  75                  80

Thr Asn Ala Ile Glu Asn Gly Ala Thr Glu Val Asp Met Val Ile Asn
                85                  90                  95

Ile Gly Ala Leu Lys Asp Lys Gln Tyr Glu Leu Val Gly Arg Asp Ile
            100                 105                 110

Gln Ala Val Val Lys Ala Ala Glu Gly Lys Ala Leu Thr Lys Val Ile
        115                 120                 125

Ile Glu Thr Ser Leu Leu Thr Glu Glu Lys Lys Ala Ala Cys Glu
    130                 135                 140

Leu Ala Val Lys Ala Gly Ala Asp Phe Val Lys Thr Ser Thr Gly Phe
145                 150                 155                 160

Ser Gly Gly Gly Ala Thr Ala Glu Asp Ile Ala Leu Met Arg Lys Val
                165                 170                 175

Val Gly Pro Asn Leu Gly Val Lys Ala Ser Gly Gly Val Arg Asp Leu
            180                 185                 190

Ser Asp Ala Lys Ala Met Ile Asp Ala Gly Ala Thr Arg Ile Gly Ala
        195                 200                 205

Ser Ala Gly Val Ala Ile Val Asn Gly Glu Arg Ser Glu Gly Ser Tyr
    210                 215                 220
```

<210> SEQ ID NO 34
<211> LENGTH: 672
<212> TYPE: DNA
<213> ORGANISM: Bacillus licheniformis

<400> SEQUENCE: 34

```
atgacaaaac aaattgcgcg aatgatcgat cacactgcat tgaagccaga taccgtcaaa      60
```

```
tccgaaatcg aagcgctttg caaagaagcg cgtgtttacg gttttgcctc cgtttgtgtc    120
aacccttgct gggtgaagct tgcgccgag cttcttaaag agtcagaggt gaaagtatgt     180
acagttatcg gctttccttt aggtgcagcg tctccggaaa caaaagcctt tgaaaccagg    240
caggcaattg cagacggtgc cggtgaagtt gatatggtga tcaacatcgg tgcactaaaa    300
gaccgcgata cgggaacagt ggaacatgac atcagggcgg tgacagacgc ggccgacggc    360
aaagctcttg taaaagtcat catagagacg tcgcttttga cggatgaaga aaaaaggctg    420
gcttgtgaac tggccgtaaa agcaggcgcc gactttgtca aaacatcgac cggttttttcc   480
ggcggcggtg cgacagtccg ggatataaaa ctgatgcggg aagctgtcgg acctgatatc    540
ggcgttaaag cttcaggtgg cgtccgcgat aaggaaagcg cacttgccat gattgaagcc    600
ggagcgacga aatcggagc gagcgccggc gtgtcgattg tcaaagggtt aacagcggat     660
gaagactact aa                                                        672
```

<210> SEQ ID NO 35
<211> LENGTH: 223
<212> TYPE: PRT
<213> ORGANISM: Bacillus licheniformis

<400> SEQUENCE: 35

```
Met Thr Lys Gln Ile Ala Arg Met Ile Asp His Thr Ala Leu Lys Pro
  1               5                  10                  15

Asp Thr Val Lys Ser Glu Ile Glu Ala Leu Cys Lys Glu Ala Arg Val
             20                  25                  30

Tyr Gly Phe Ala Ser Val Cys Val Asn Pro Cys Trp Val Lys Leu Cys
         35                  40                  45

Ala Glu Leu Leu Lys Glu Ser Glu Val Lys Val Cys Thr Val Ile Gly
     50                  55                  60

Phe Pro Leu Gly Ala Ala Ser Pro Glu Thr Lys Ala Phe Glu Thr Arg
 65                  70                  75                  80

Gln Ala Ile Ala Asp Gly Ala Gly Glu Val Asp Met Val Ile Asn Ile
                 85                  90                  95

Gly Ala Leu Lys Asp Arg Asp Thr Gly Thr Val Glu His Asp Ile Arg
            100                 105                 110

Ala Val Thr Asp Ala Ala Asp Gly Lys Ala Leu Val Lys Val Ile Ile
        115                 120                 125

Glu Thr Ser Leu Leu Thr Asp Glu Glu Lys Arg Leu Ala Cys Glu Leu
    130                 135                 140

Ala Val Lys Ala Gly Ala Asp Phe Val Lys Thr Ser Thr Gly Phe Ser
145                 150                 155                 160

Gly Gly Gly Ala Thr Val Arg Asp Ile Lys Leu Met Arg Glu Ala Val
                165                 170                 175

Gly Pro Asp Ile Gly Val Lys Ala Ser Gly Gly Val Arg Asp Lys Glu
            180                 185                 190

Ser Ala Leu Ala Met Ile Glu Ala Gly Ala Thr Arg Ile Gly Ala Ser
        195                 200                 205

Ala Gly Val Ser Ile Val Lys Gly Leu Thr Ala Asp Glu Asp Tyr
    210                 215                 220
```

<210> SEQ ID NO 36
<211> LENGTH: 663
<212> TYPE: DNA
<213> ORGANISM: Streptococcus mutans

<400> SEQUENCE: 36

```
atgaaaatca atcaatatat tgaccatact ttattaaaac cagaaagtag gcaagatcag      60
attgataaac tgattcgaga agctaagaca tataattttg ccagtgtctg tatcaatcca     120
acttgggttt cttatgcggc taaagctctt gaaggaacag acattaaagt ttgtactgtt     180
attggttttc ctttaggagc aacgactagt gctgtaaaag cctttgaaac caaggatgct     240
attagtcatg gagctgacga agttgatatg gttatcaata ttggtcaagc taaatctggt     300
cattttgctt ttgttgaaga agatattcgg gcagttgttg aagccagtgg tgacaaattg     360
gtgaaagtta ttattgaaac ttgtctcctt acagataaag aaaaaattaa agcttgtcaa     420
gctgcagtag cagcaggtgc tgatttcgtt aaaacatcaa ctggttttc aactgctgga      480 gctaggttag atgatgttcg tcttatgcgt caaacggtag gacctgatgt tggagtaaag     540
gcggcaggag gaacgcgatc tttagaagat gcgcaagctt ttattgaagc aggtgcaaca     600
cgtattggga catctgctgg agttactatt atggaaggaa agcaaacaaa cagtggttat     660
tga                                                                  663
```

<210> SEQ ID NO 37
<211> LENGTH: 220
<212> TYPE: PRT
<213> ORGANISM: Streptococcus mutans

<400> SEQUENCE: 37

```
Met Lys Ile Asn Gln Tyr Ile Asp His Thr Leu Leu Lys Pro Glu Ser
1               5                   10                  15

Arg Gln Asp Gln Ile Asp Lys Leu Ile Arg Glu Ala Lys Thr Tyr Asn
            20                  25                  30

Phe Ala Ser Val Cys Ile Asn Pro Thr Trp Val Ser Tyr Ala Ala Lys
        35                  40                  45

Ala Leu Glu Gly Thr Asp Ile Lys Val Cys Thr Val Ile Gly Phe Pro
    50                  55                  60

Leu Gly Ala Thr Thr Ser Ala Val Lys Ala Phe Glu Thr Lys Asp Ala
65                  70                  75                  80

Ile Ser His Gly Ala Asp Glu Val Asp Met Val Ile Asn Ile Gly Gln
                85                  90                  95

Ala Lys Ser Gly His Phe Ala Phe Val Glu Glu Asp Ile Arg Ala Val
            100                 105                 110

Val Glu Ala Ser Gly Asp Lys Leu Val Lys Val Ile Ile Glu Thr Cys
        115                 120                 125

Leu Leu Thr Asp Lys Glu Lys Ile Lys Ala Cys Gln Ala Ala Val Ala
    130                 135                 140

Ala Gly Ala Asp Phe Val Lys Thr Ser Thr Gly Phe Ser Thr Ala Gly
145                 150                 155                 160

Ala Arg Leu Asp Asp Val Arg Leu Met Arg Gln Thr Val Gly Pro Asp
                165                 170                 175

Val Gly Val Lys Ala Ala Gly Gly Thr Arg Ser Leu Glu Asp Ala Gln
            180                 185                 190

Ala Phe Ile Glu Ala Gly Ala Thr Arg Ile Gly Thr Ser Ala Gly Val
        195                 200                 205

Thr Ile Met Glu Gly Lys Gln Thr Asn Ser Gly Tyr
    210                 215                 220
```

<210> SEQ ID NO 38
<211> LENGTH: 663
<212> TYPE: DNA
<213> ORGANISM: Staphylococcus epidermidis

<400> SEQUENCE: 38

```
atgaataaag caaaattgat agaccataca ttattaaaac ctgattcaac aaaggaacaa    60
atagatacta ttataaatga agcaaaagca tatcagttta agtctgtatg tgtgaaccct   120
acacatgtac aatatgcatc tgaacaactt aaaggaacag acgttttagt gtgtactgtt   180
attggatttc cactaggtgc aacaactaca gcggttaaat cttatgaaac aaaagatgcg   240
attaacaatg gtgcccaaga gattgatatg gtgataaata ttggagcact taaggatggc   300
cgttttgatg aagtgcaaaa tgatatcgaa gccgtcgttc aagcagccaa tggtaaaaca   360
gttaaggtaa ttattgagac tgtttttatta actgagaaag agaagattaa agcatgtcaa   420
ttatctgaag cggcaggtgc acattttgtt aaaacatcca caggttttgc tggtgggggt   480
gcaacagttg aagatgtaaa attaatgaaa gatactgttg tgatcgtttt agaagtaaaa   540
gcgtcaggcg gcgtgagaaa tctagaagat tttaataata tgattgaagc gggtgctaca   600
cgtattggtg ctagtgccgg tgtgcaaatt attcaaggac ttgaatcaaa tactgattac   660
taa                                                                 663
```

<210> SEQ ID NO 39
<211> LENGTH: 220
<212> TYPE: PRT
<213> ORGANISM: Staphylococcus epidermidis

<400> SEQUENCE: 39

```
Met Asn Lys Ala Lys Leu Ile Asp His Thr Leu Leu Lys Pro Asp Ser
1               5                   10                  15
Thr Lys Glu Gln Ile Asp Thr Ile Ile Asn Glu Ala Lys Ala Tyr Gln
                20                  25                  30
Phe Lys Ser Val Cys Val Asn Pro Thr His Val Gln Tyr Ala Ser Glu
            35                  40                  45
Gln Leu Lys Gly Thr Asp Val Leu Val Cys Thr Val Ile Gly Phe Pro
        50                  55                  60
Leu Gly Ala Thr Thr Thr Ala Val Lys Ser Tyr Glu Thr Lys Asp Ala
65                  70                  75                  80
Ile Asn Asn Gly Ala Gln Glu Ile Asp Met Val Ile Asn Ile Gly Ala
                85                  90                  95
Leu Lys Asp Gly Arg Phe Asp Glu Val Gln Asn Asp Ile Glu Ala Val
            100                 105                 110
Val Gln Ala Ala Asn Gly Lys Thr Val Lys Val Ile Glu Thr Val
        115                 120                 125
Leu Leu Thr Glu Lys Glu Lys Ile Lys Ala Cys Gln Leu Ser Glu Ala
130                 135                 140
Ala Gly Ala His Phe Val Lys Thr Ser Thr Gly Phe Ala Gly Gly Gly
145                 150                 155                 160
Ala Thr Val Glu Asp Val Lys Leu Met Lys Asp Thr Val Gly Asp Arg
                165                 170                 175
Leu Glu Val Lys Ala Ser Gly Gly Val Arg Asn Leu Glu Asp Phe Asn
            180                 185                 190
Asn Met Ile Glu Ala Gly Ala Thr Arg Ile Gly Ala Ser Ala Gly Val
        195                 200                 205
Gln Ile Ile Gln Gly Leu Glu Ser Asn Thr Asp Tyr
    210                 215                 220
```

<210> SEQ ID NO 40
<211> LENGTH: 648

<212> TYPE: DNA
<213> ORGANISM: Lactobacillus plantarum

<400> SEQUENCE: 40

```
atgaaattga atcgttattt agatcacacg ttattaaaac cggaagcgac tgagcaacaa    60
attgatcagg tagtacggga ggcactcgaa aatcactttt attcagttat ggtcaatcca   120
tactgggtca agcacgtcca tgcgcaactt gctggttcgg atgttgcgac tgcatgcgtg   180
attggtttcc ctctgggcgc gaatacaacc gccattaaag ttgcggaagc caaacaggca   240
attgctgacg gtgtggatga gctggatatg gtcattaata tcggcgaatt gaaaggcgac   300
cactatgatg cagttcaaca agacattgaa agtgtggtaa cagttggaca tacggctgat   360
aaggtcgtca agtgattat tgaaacggcg ctgttgacgg atggggaaat cgttaaggct   420
agtgaaattg ttgccgatgc acacgctgat tttgtgaaga catcgactgg attttcaacc   480
cgtggtgctt cggttcatga tattagtttg atgaagggtg ccgttcagga tcgaatcggg   540
gtcaaagcat ctgggggaat ccatacacgc gatgaagcat tagcgatgat tgatgctgga   600
gcaacgcgcc tcggtgtatc agcaagtatg gcaattattg gtaagtag              648
```

<210> SEQ ID NO 41
<211> LENGTH: 215
<212> TYPE: PRT
<213> ORGANISM: Lactobacillus plantarum

<400> SEQUENCE: 41

```
Met Lys Leu Asn Arg Tyr Leu Asp His Thr Leu Leu Lys Pro Glu Ala
1               5                   10                  15

Thr Glu Gln Gln Ile Asp Gln Val Val Arg Glu Ala Leu Glu Asn His
            20                  25                  30

Phe Tyr Ser Val Met Val Asn Pro Tyr Trp Val Lys His Val His Ala
        35                  40                  45

Gln Leu Ala Gly Ser Asp Val Ala Thr Ala Cys Val Ile Gly Phe Pro
    50                  55                  60

Leu Gly Ala Asn Thr Thr Ala Ile Lys Val Ala Glu Ala Lys Gln Ala
65                  70                  75                  80

Ile Ala Asp Gly Val Asp Glu Leu Asp Met Val Ile Asn Ile Gly Glu
                85                  90                  95

Leu Lys Gly Asp His Tyr Asp Ala Val Gln Gln Asp Ile Glu Ser Val
            100                 105                 110

Val Thr Val Gly His Thr Ala Asp Lys Val Val Lys Val Ile Glu
        115                 120                 125

Thr Ala Leu Leu Thr Asp Gly Glu Ile Val Lys Ala Ser Glu Ile Val
    130                 135                 140

Ala Asp Ala His Ala Asp Phe Val Lys Thr Ser Thr Gly Phe Ser Thr
145                 150                 155                 160

Arg Gly Ala Ser Val His Asp Ile Ser Leu Met Lys Gly Ala Val Gln
                165                 170                 175

Asp Arg Ile Gly Val Lys Ala Ser Gly Gly Ile His Thr Arg Asp Glu
            180                 185                 190

Ala Leu Ala Met Ile Asp Ala Gly Ala Thr Arg Leu Gly Val Ser Ala
        195                 200                 205

Ser Met Ala Ile Ile Gly Lys
    210                 215
```

<210> SEQ ID NO 42
<211> LENGTH: 728

<212> TYPE: DNA
<213> ORGANISM: Lactobacillus acidophilus

<400> SEQUENCE: 42

```
cagaggtaaa aattatgaaa tatactttag acgactttgc acgtttaatt gatcacacta    60
acttacacgc tgatgcaact gaagccgata tgaagaagtt atgtgatgaa gcaaagaaat   120
atcattttaa aatggtagct attaatcaag ttcaatccaa gttttgctca gagcaattaa   180
agggaacaga cattgatact ggtgctgcaa ttgcttttcc tttaggacaa caaactattg   240
aatccaaggt atttgatact agggatgcaa ttaagaatgg tgctaatgaa attgattatg   300
tgattaatat tactcaatta aaagctaaag actacgatta tataaagcaa gaaatgcaag   360
agatggttaa tgcttgtcat gaaaatcatg ttccatgtaa agtgattttt gaaaattgct   420
atttaaccaa agatgaaata aaaaaattag ctgagattgc taagaagta aagcctgact    480
ttattaagac ttctactggc tttggtagtt caggcgctaa ggtagaagac gtaaagctaa   540
tgaaatcaat tgttggcgat gaagtaaaag taaaggctgc cggtggtatt cgtaatagtg   600
atgatttctt agccatggtg cgcgctggtg ctgatagaat tggttgttct gctggagtca   660
aaatttatca gctttaaaag tgtagaatga aagacgacca tgtggatagt attgagattg   720
cacgttag                                                            728
```

<210> SEQ ID NO 43
<211> LENGTH: 237
<212> TYPE: PRT
<213> ORGANISM: Lactobacillus acidophilus

<400> SEQUENCE: 43

```
Met Lys Tyr Thr Leu Asp Asp Phe Ala Arg Leu Ile Asp His Thr Asn
1               5                   10                  15

Leu His Ala Asp Ala Thr Glu Ala Asp Met Lys Lys Leu Cys Asp Glu
            20                  25                  30

Ala Lys Lys Tyr His Phe Lys Met Val Ala Ile Asn Gln Val Gln Ser
        35                  40                  45

Lys Phe Cys Ser Glu Gln Leu Lys Gly Thr Asp Ile Asp Thr Gly Ala
    50                  55                  60

Ala Ile Ala Phe Pro Leu Gly Gln Gln Thr Ile Glu Ser Lys Val Phe
65                  70                  75                  80

Asp Thr Arg Asp Ala Ile Lys Asn Gly Ala Asn Glu Ile Asp Tyr Val
                85                  90                  95

Ile Asn Ile Thr Gln Leu Lys Ala Lys Asp Tyr Asp Tyr Ile Lys Gln
            100                 105                 110

Glu Met Gln Glu Met Val Asn Ala Cys His Glu Asn His Val Pro Cys
        115                 120                 125

Lys Val Ile Phe Glu Asn Cys Tyr Leu Thr Asp Glu Ile Lys Lys
    130                 135                 140

Leu Ala Glu Ile Ala Lys Glu Val Lys Pro Asp Phe Ile Lys Thr Ser
145                 150                 155                 160

Thr Gly Phe Gly Ser Ser Gly Ala Lys Val Glu Asp Val Lys Leu Met
                165                 170                 175

Lys Ser Ile Val Gly Asp Glu Val Lys Val Lys Ala Ala Gly Gly Ile
            180                 185                 190

Arg Asn Ser Asp Asp Phe Leu Ala Met Val Arg Ala Gly Ala Asp Arg
        195                 200                 205

Ile Gly Cys Ser Ala Gly Val Ile Tyr Gln Ala Leu Lys Cys Arg
    210                 215                 220
```

Met Lys Asp Asp His Val Asp Ser Ile Glu Ile Ala Arg
225                 230                 235

<210> SEQ ID NO 44
<211> LENGTH: 672
<212> TYPE: DNA
<213> ORGANISM: Streptococcus pyogenes

<400> SEQUENCE: 44
gtggaagtaa aagatatttt aaaaacggta gaccatactt tgctagcaac aacagcaacg     60
tggccagaaa tccaaacaat tttagatgat gccatggctt atgaaacagc ttcagcatgt    120
attccagctt cttacgtcaa aaaagcagca gaatacgttt caggtaaatt agctatttgt    180
actgttattg ggttcccaaa tggctatagt acaactgcgg cgaaggtttt tgaatgtcaa    240
gatgctattc aaaatggtgc tgatgaaatt gacatggtca ttaatttgac agacgttaaa    300 aatgggatt tgatactgt tgaagaagaa attcgtcaaa tcaaagctaa atgtcaagac    360
catatcttaa aagttatcgt tgagacatgt caattaacta agaagaact tatcgaactt    420 tgtggagttg tcacacgttc aggtgcagac tttattaaaa cctctactgg ttttttcgaca    480 gcaggtgcta catttgaaga tgttgaagtg atggcaaaat atgtcggcga aggtgttaaa    540
attaaggcag caggtggaat ctcatcattg gaagatgcta aaacatttat tgctttagga    600
gcttcacgct tgggtactag ccgtatcatc aagattgtta agaacgaagc tacaaaaccc    660
gatagctatt aa                                                         672

<210> SEQ ID NO 45
<211> LENGTH: 223
<212> TYPE: PRT
<213> ORGANISM: Streptococcus pyogenes

<400> SEQUENCE: 45

Met Glu Val Lys Asp Ile Leu Lys Thr Val Asp His Thr Leu Ala
1               5                   10                  15

Thr Thr Ala Thr Trp Pro Glu Ile Gln Thr Ile Leu Asp Asp Ala Met
                20                  25                  30

Ala Tyr Glu Thr Ala Ser Ala Cys Ile Pro Ala Ser Tyr Val Lys Lys
            35                  40                  45

Ala Ala Glu Tyr Val Ser Gly Lys Leu Ala Ile Cys Thr Val Ile Gly
        50                  55                  60

Phe Pro Asn Gly Tyr Ser Thr Thr Ala Ala Lys Val Phe Glu Cys Gln
65                  70                  75                  80

Asp Ala Ile Gln Asn Gly Ala Asp Glu Ile Asp Met Val Ile Asn Leu
                85                  90                  95

Thr Asp Val Lys Asn Gly Asp Phe Asp Thr Val Glu Glu Glu Ile Arg
            100                 105                 110

Gln Ile Lys Ala Lys Cys Gln Asp His Ile Leu Lys Val Ile Val Glu
        115                 120                 125

Thr Cys Gln Leu Thr Lys Glu Glu Leu Ile Glu Leu Cys Gly Val Val
    130                 135                 140

Thr Arg Ser Gly Ala Asp Phe Ile Lys Thr Ser Thr Gly Phe Ser Thr
145                 150                 155                 160

Ala Gly Ala Thr Phe Glu Asp Val Glu Val Met Ala Lys Tyr Val Gly
                165                 170                 175

Glu Gly Val Lys Ile Lys Ala Ala Gly Gly Ile Ser Ser Leu Glu Asp
            180                 185                 190

```
Ala Lys Thr Phe Ile Ala Leu Gly Ala Ser Arg Leu Gly Thr Ser Arg
        195                 200                 205

Ile Ile Lys Ile Val Lys Asn Glu Ala Thr Lys Pro Asp Ser Tyr
    210                 215                 220
```

<210> SEQ ID NO 46
<211> LENGTH: 783
<212> TYPE: DNA
<213> ORGANISM: Rhodopirellula baltica

<400> SEQUENCE: 46

```
ttgcgcgaca cccgacctcc tgccgcatcg ctatcgcttc acggaaacct gctcaccatg      60
gctgactatc aatatcacga cgtctccaag atgattgacc actcgctgct tccacccaca     120
ctgaccgaag cggacttgga ttccggcatc gatttggcaa tcgcttatga agtcgccagc     180
gtttgtatct tgccctacta cttgaaacgt tgtgctgcga agctcgcggg caccggcgtg     240
aaagcgtcaa ccacgatcgg ttttcctcat ggtggtcaca ccaccgcgat caagaaagcc     300
gaagccgaac aagccatcca agatggctgc gaagaactcg acttcgtcgt caacatctcg     360
caagtcctga gcggcggttg ggactacgtc aaaatgaaaa ttggcgaggt caccgaactg     420
acccatgcgg ccggacaaaa gatcaaggtg atcttcgaga actgctacct gcaggacgaa     480
cacaagattc gtctgtgcga gatctgcacc gagctcaaag tggactgggt caaaacatcg     540
actggttatg aactggaggc gcgaccatg  gacgacctgc gtctgatgcg acaacactca     600
ggcgaaaacg tccaagtcaa agctgccggt ggcgtccgag atctcgcgac actgctggag     660
gtccgagccc tcggagcatc ccgttgcggt gccagccgaa ccgccgagat gctgggcgaa     720
gcccgaaagc aacttggcat gcccgcgatt gaaatcaccg cgaccggcag ctccggctac     780
tga                                                                    783
```

<210> SEQ ID NO 47
<211> LENGTH: 260
<212> TYPE: PRT
<213> ORGANISM: Rhodopirellula baltica

<400> SEQUENCE: 47

```
Met Arg Asp Thr Arg Pro Pro Ala Ala Ser Leu Ser Leu His Gly Asn
1               5                   10                  15

Leu Leu Thr Met Ala Asp Tyr Gln Tyr His Asp Val Ser Lys Met Ile
            20                  25                  30

Asp His Ser Leu Leu Pro Pro Thr Leu Thr Glu Ala Asp Leu Asp Ser
        35                  40                  45

Gly Ile Asp Leu Ala Ile Ala Tyr Glu Val Ala Ser Val Cys Ile Leu
    50                  55                  60

Pro Tyr Tyr Leu Lys Arg Cys Ala Ala Lys Leu Ala Gly Thr Gly Val
65                  70                  75                  80

Lys Ala Ser Thr Thr Ile Gly Phe Pro His Gly His Thr Thr Ala
                85                  90                  95

Ile Lys Lys Ala Glu Ala Glu Gln Ala Ile Gln Asp Gly Cys Glu Glu
            100                 105                 110

Leu Asp Phe Val Val Asn Ile Ser Gln Val Leu Ser Gly Gly Trp Asp
        115                 120                 125

Tyr Val Gln Asn Glu Ile Gly Glu Val Thr Glu Leu Thr His Ala Ala
    130                 135                 140

Gly Gln Lys Ile Lys Val Ile Phe Glu Asn Cys Tyr Leu Gln Asp Glu
145                 150                 155                 160
```

```
His Lys Ile Arg Leu Cys Glu Ile Cys Thr Glu Leu Lys Val Asp Trp
                165                 170                 175

Val Lys Thr Ser Thr Gly Tyr Gly Thr Gly Gly Ala Thr Met Asp Asp
            180                 185                 190

Leu Arg Leu Met Arg Gln His Ser Gly Glu Asn Val Gln Val Lys Ala
        195                 200                 205

Ala Gly Gly Val Arg Asp Leu Ala Thr Leu Leu Glu Val Arg Ala Leu
    210                 215                 220

Gly Ala Ser Arg Cys Gly Ala Ser Arg Thr Ala Glu Met Leu Gly Glu
225                 230                 235                 240

Ala Arg Lys Gln Leu Gly Met Pro Ala Ile Glu Ile Thr Ala Thr Gly
                245                 250                 255

Ser Ser Gly Tyr
            260

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgggatccac tgatctgaaa gcaagcagcc                                          30

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcaagcttgc tgctggcgct cttacc                                              26
```